(12) United States Patent
Pendleton et al.

(10) Patent No.: US 11,642,139 B2
(45) Date of Patent: May 9, 2023

(54) ACETABULAR AND GLENOID REAMER SYSTEMS AND METHODS USING THE SAME

(71) Applicant: ORIGIN MEDICAL, LLC., Atlanta, GA (US)

(72) Inventors: John E. Pendleton, Atlanta, GA (US); Daniel H. Hursh, Roswell, GA (US)

(73) Assignee: ORIGIN MEDICAL, LLC., Atlanta, GA (US)

( * ) Notice: Subject to any disclaimer, the term of this patent is extended or adjusted under 35 U.S.C. 154(b) by 238 days.

(21) Appl. No.: 17/178,713

(22) Filed: Feb. 18, 2021

(65) Prior Publication Data

US 2021/0275192 A1 Sep. 9, 2021

Related U.S. Application Data

(60) Provisional application No. 63/198,525, filed on Oct. 25, 2020, provisional application No. 62/985,747, filed on Mar. 5, 2020.

(51) Int. Cl.
*A61B 17/16* (2006.01)
*A61B 17/17* (2006.01)
*A61B 34/30* (2016.01)

(52) U.S. Cl.
CPC ...... *A61B 17/1626* (2013.01); *A61B 17/1666* (2013.01); *A61B 17/1746* (2013.01); *A61B 34/30* (2016.02)

(58) Field of Classification Search
CPC ... A61B 17/16; A61B 17/1613; A61B 17/162; A61B 17/1624; A61B 17/1626; A61B 17/1628; A61B 17/1631; A61B 17/1659; A61B 17/1662; A61B 17/1664; A61B 17/1666; A61B 17/1684; A61B 17/1746; A61B 17/1778
See application file for complete search history.

(56) References Cited

U.S. PATENT DOCUMENTS

| | | | |
|---|---|---|---|
| 5,658,290 A | 8/1997 | Lechot | |
| 5,919,195 A * | 7/1999 | Wilson | A61B 17/1666 606/81 |
| 6,854,742 B2 | 2/2005 | Salyer | |
| 7,115,119 B2 | 10/2006 | Desarzens | |
| 7,993,348 B2 * | 8/2011 | Conte | A61B 17/1631 606/81 |
| 8,475,460 B1 * | 7/2013 | Roger | A61B 17/1666 606/81 |
| 9,078,672 B1 * | 7/2015 | Rosse | A61B 17/1631 |
| 9,173,663 B2 | 11/2015 | Ryall et al. | |
| 2004/0153080 A1 * | 8/2004 | Dong | A61B 17/1666 606/80 |
| 2005/0216022 A1 * | 9/2005 | Lechot | A61B 17/1666 606/81 |

(Continued)

FOREIGN PATENT DOCUMENTS

WO WO-2019161985 A1 * 8/2019 ......... A61B 17/1631
WO WO-2021174347 A1 * 9/2021 ......... A61B 17/1659

*Primary Examiner* — Eric S Gibson
(74) *Attorney, Agent, or Firm* — FisherBroyles, LLP; Anthony Dovale; John Boyd

(57) ABSTRACT

Tools for cutting bone, specifically cutting a hemispherical cavity in bone. Preferably, tools including an adaptor device configured to provide independent control of the cutting orientation.

22 Claims, 11 Drawing Sheets

(56) References Cited

U.S. PATENT DOCUMENTS

| | | | |
|---|---|---|---|
| 2008/0058804 A1* | 3/2008 | Lechot | A61B 17/1631 606/53 |
| 2013/0331841 A1* | 12/2013 | Roger | A61B 17/1664 606/80 |
| 2015/0005776 A1* | 1/2015 | Biegun | A61B 17/1633 606/85 |
| 2015/0119891 A1 | 4/2015 | Goldberg et al. | |
| 2016/0278939 A1* | 9/2016 | Siccardi | A61B 17/1666 |
| 2021/0015494 A1* | 1/2021 | Flatters | A61B 17/1631 |
| 2021/0267609 A1* | 9/2021 | Nguyen | A61B 90/50 |
| 2021/0275192 A1* | 9/2021 | Pendleton | A61B 17/1626 |

\* cited by examiner

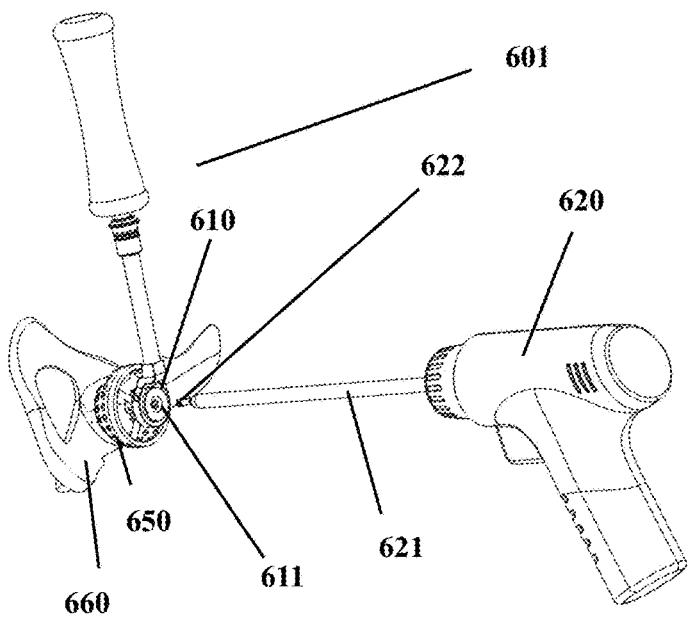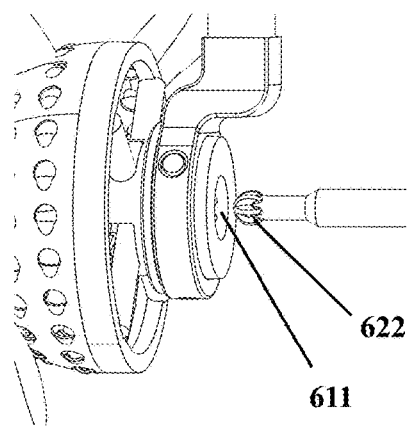
FIG. 6A
FIG. 6B
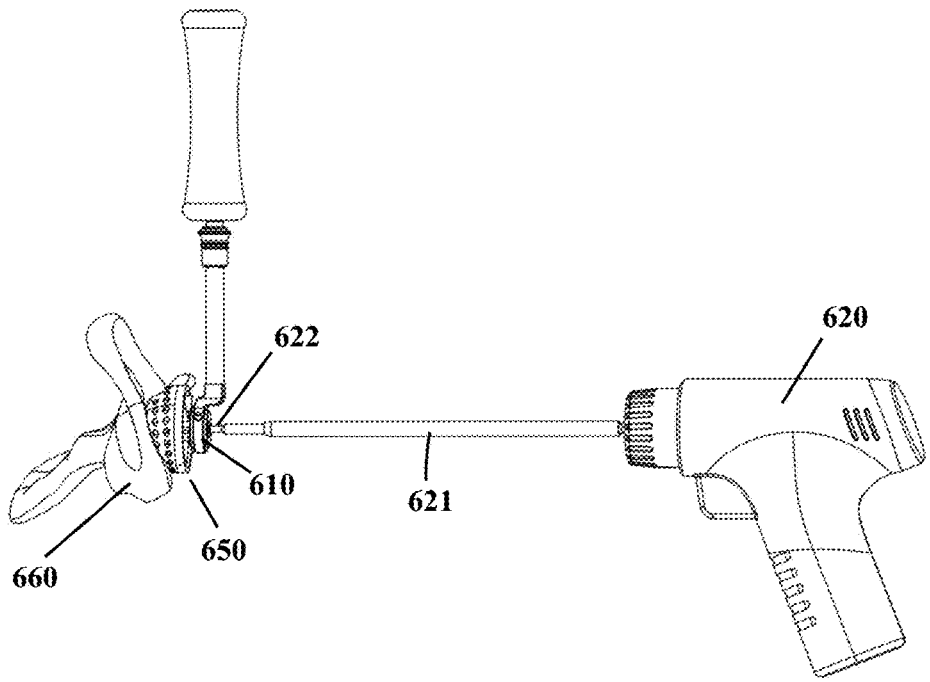
FIG. 6C

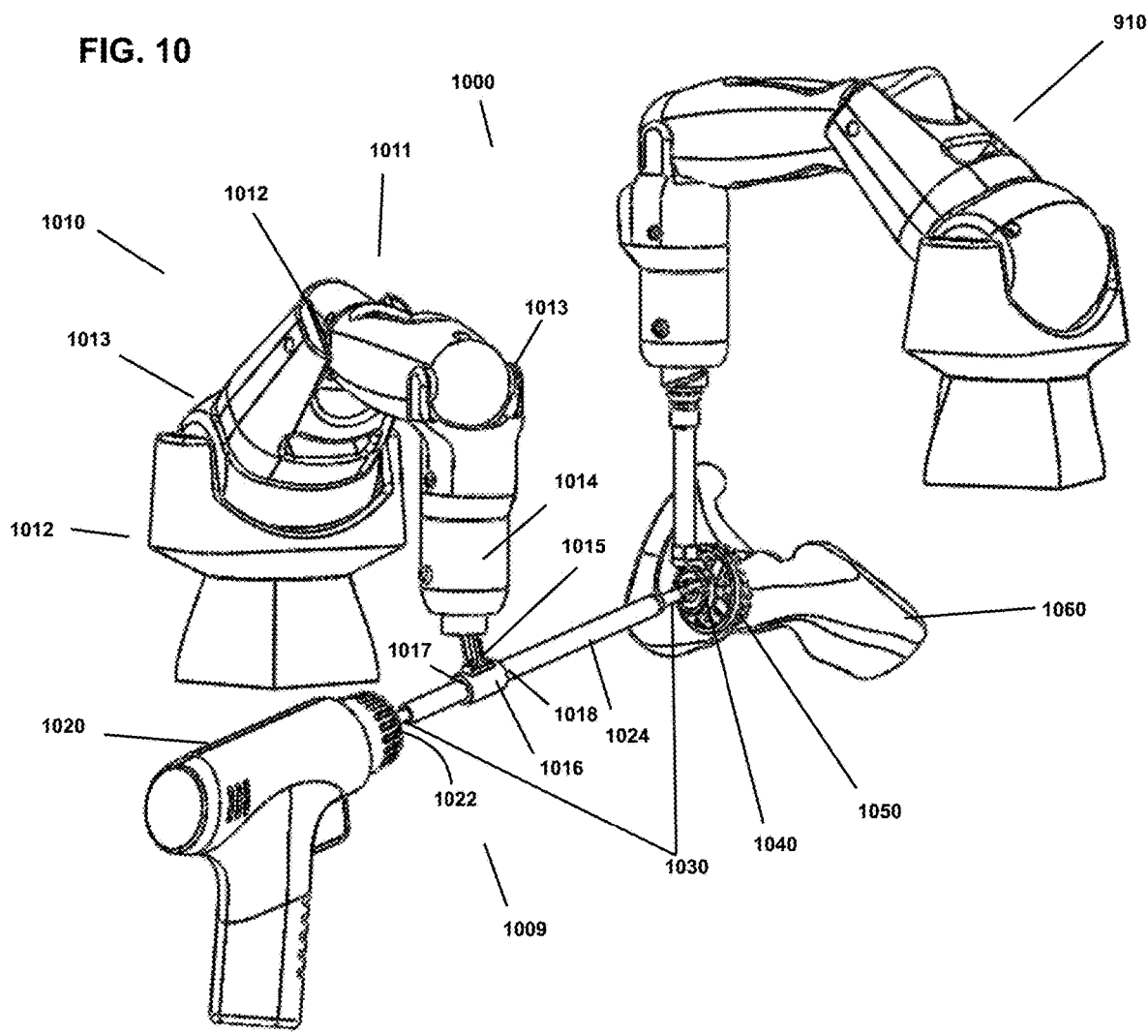

ACETABULAR AND GLENOID REAMER SYSTEMS AND METHODS USING THE SAME

RELATED APPLICATIONS

This application claims the benefit of and priority to U.S. Provisional Application No. 63/198,525 entitled "ACETABULAR AND GLENOID REAMER SYSTEM AND METHODS USING THE SAME" filed Oct. 25, 2020 and U.S. Provisional Application No. 62/985,747 entitled "ACETABULAR AND GLENOID REAMER SYSTEMS AND METHODS USING THE SAME" filed Mar. 5, 2020, each hereby incorporated by reference in its entirety.

FIELD OF THE INVENTION

The present invention relates generally to improved tools for cutting bone, specifically cutting a hemispherical cavity in bone and preferably tools including an adaptor device configured to provide independent control of the cutting orientation and systems including the same.

BACKGROUND OF THE INVENTION

Several publications are referenced in this application. The cited references describe the state of the art to which this invention pertains and are hereby incorporated by reference, particularly the devices, systems, components, and methods set forth in the detailed description and figures of each reference.

Acetabular/Glenoid reaming systems are well known in hip/shoulder arthroplasty, to prepare bone tissue for receiving a hemispherical implant. In the field of orthopaedic surgery, it is often necessary to remove bone material to enable implantation of prosthesis to repair joints in the human body.

Acetabular reamer cups and glenoid reamers are surgical tools which are used in surgery for the insertion of artificial joints. Acetabular reamer cups are used to cut hemispherical cavities in pelvis bones for the insertion of artificial hip joints. Glenoid reamers are used to cut hemispherical cavities in shoulder bones for the insertion of artificial shoulder joints. Acetabular reamer cups and glenoid reamers have a complex arrangement of cutting edges arranged on a spherical surface around the axis of rotation of the cup.

A number of tools have been developed for this purpose and include reamers having generally semi-hemispherical configuration with cutting elements on them so that a corresponding semi-hemispherical hollow can be formed in the bone material for providing a foundation for the repair of the joint.

Typically, surgeons use specialized drivers attached to the reamers. The drivers connect to a source of power and have appropriate handles for guiding the operation of the reamer by a surgeon. An example of a straight driver for this type is found in U.S. Pat. No. 5,658,290 in which a bayonet interconnection is provided between the reamer and the driver. An example of an offset version of a driver handle is found in U.S. Pat. No. 7,993,348 in which the handle is offset or curved in order avoid impingement with surrounding tissues or other instruments.

Additionally, there are currently various reamer connection configurations or styles in the field, one of which is for the Othy style manufactured by Symmetry Medical, Inc. and the other style manufactured by Precimed SA of L'Echelette, Switzerland. Although these both have semi hemispherical cutting heads, they have different interfaces between driving tools with which they are associated. The Othy style has a crossbridge element—this element is a bar extending between the circumference of the hemisphere and having a circular expanded section in the middle. Numerous arrangements are available for securing this device as exemplified by U.S. Pat. No. 6,854,742. Alternatively, the Precimed reamer has a crossbar shape in which two circular cross section bars intersect at the center and extend to the walls of the hemisphere.

SUMMARY OF THE INVENTION

The invention relates to adaptors for use with bone reaming, abrading, cutting, and other bone modifying systems and methods of using the same. Preferably, the present invention relates to orthopedic surgical reamers and more specifically relates to adaptor housing and drivers for such tools.

One aspect of the invention relates to an adaptor device for a bone cutting system, the adaptor device comprising:
  (a) an adaptor head configured to reversibly connect to a bone cutter and further configured to reversibly engage with a bone cutter driver; and
  (b) an adaptor housing configured to connect to the adaptor head and further configured to attach to a handle and/or a robotic arm for the adaptor device.

One embodiment of the invention relates to systems comprising two main functional elements: (i) an adaptor that connects to a reamer or reamer basket and also connects to a handle and/or robotic arm; and (ii) a driver shaft with a driver tip (e.g., ball nosed driver tip) to allow for engagement with the adaptor to operate the reamer at variable angles. The system advantageously allows for independent orientation (preferably rotation in all planes) of the reamer via the adaptor and handle/robotic arm relative to the driver shaft.

According to an alternative embodiment, the system comprises an adaptor device that connects to a reamer or reamer basket and is also connected to at least one robotic arm, wherein the at least one robotic arm includes a reamer driver adapted for engagement with the adapter device to operate and drive the reamer at variable angles. The system advantageously allows for independent orientation (preferably rotation in all planes) of the reamer via the adaptor device and robotic arm relative to the bone surface being subject to reaming.

Another embodiment of the invention relates to an adaptor device for an arthroplasty reaming system, the adaptor device comprising:
  (a) an adaptor head configured to reversibly connect to a reamer and further configured to reversibly engage with a reamer driver; and
  (b) an adaptor housing configured to connect to the adaptor head and further configured to attach to a handle for the adaptor device and/or at least one robotic arm for the adaptor device.

Another embodiment of the invention relates to an arthroplasty reaming system comprising one or more of the adaptor devices described herein and a reamer driver.

Another embodiment of the invention relates to an arthroplasty reaming system comprising one or more of the adaptor devices described herein and a reamer.

Another embodiment of the invention relates to an arthroplasty reaming system comprising one or more adaptor devices as described herein, a reamer driver and a guide arm connected to a handle and reamer driver.

Another embodiment of the invention relates to an arthroplasty reaming system comprising one or more adaptor devices as described herein, a reamer driver and at least one robotic arm configured to be connected to the one or more adaptor devices and, optionally, connected to the reamer driver or comprising the reamer driver.

Another embodiment of the invention relates to an arthroplasty reaming system comprising one or more adaptor devices as described herein, a reamer, a reamer driver and a guide arm connected to a handle and reamer driver.

Another embodiment of the invention relates to an arthroplasty reaming system comprising one or more adaptor devices as described herein, a cannula for a reamer driver and a guide arm connected to the handle and reamer driver.

Another aspect of the invention relates to methods of using the adaptor devices described herein.

One embodiment of the invention relates to method of performing arthroplasty, the method comprising:
(a) connecting an adaptor device, preferably as described herein, to a reamer;
(b) inserting adaptor device connected to reamer into the bony anatomy;
(c) connecting a reamer driver to the adaptor device to engage the reamer;
(d) rotating the reamer with the reamer driver thereby cutting bone; and
(e) changing the orientation of the reamer relative to the reamer driver using the adapter device.

Another embodiment of the invention relates to a method of performing arthroplasty, the method comprising:
(a) inserting a reamer into a bony anatomy;
(b) connecting an adaptor device, preferably as described herein, to the reamer;
(c) connecting a reamer driver to the adaptor device to engage the reamer;
(d) rotating the reamer with the reamer driver thereby cutting bone; and
(e) changing the orientation of the reamer relative to the reamer driver using the adapter device.

Another embodiment of the invention relates to a method of performing arthroplasty, the method comprising:
(a) inserting a reamer into a bony anatomy;
(b) connecting an adaptor device, preferably as described herein, to the reamer;
(c) connecting a robotic arm to the adaptor device;
(d) connecting a reamer driver to the adaptor device to engage the reamer;
(e) rotating the reamer with the reamer driver thereby cutting bone; and
(f) changing the orientation of the reamer relative to the reamer driver using the robotic arm.

Another embodiment of the invention relates to a method of performing arthroplasty, the method comprising:
(a) connecting an adaptor device, preferably as described herein, to a reamer;
(b) inserting the reamer into a bony anatomy;
(c) connecting a robotic arm to the adaptor device;
(d) connecting a reamer driver to the adaptor device to engage the reamer;
(e) rotating the reamer with the reamer driver thereby cutting bone; and
(f) changing the orientation of the reamer relative to the reamer driver using the robotic arm.

Another embodiment of the invention relates to a method of performing arthroplasty, the method comprising:
(a) connecting an adaptor device, preferably as described herein, to a reamer;
(b) connecting a robotic arm to the adaptor device
(c) inserting the reamer into a bony anatomy;
(d) connecting a reamer driver to the adaptor device to engage the reamer;
(e) rotating the reamer with the reamer driver thereby cutting bone; and
(f) changing the orientation of the reamer relative to the reamer driver using the robotic arm.

Another embodiment of the invention relates to a method of performing arthroplasty, the method comprising:
(a) connect a handle having a handle end to an adaptor device, preferably as described herein;
(b) connect the adaptor device to a reamer;
(c) insert the handle end, the adaptor device and reamer into bony anatomy;
(d) insert a driver into the adaptor device;
(e) rotate the driver to rotate the reamer via the adaptor device;
(f) reposition the handle to re-orient the reamer while the reamer is inserted in the bony anatomy;
(g) stop rotating the driver;
(h) remove the driver from the adaptor device; and
(i) remove the handle end, the adaptor device and the reamer from the bony anatomy.

Another embodiment of the invention relates to a method of performing arthroplasty, the method comprising:
(a) connect a robotic arm having a distal end to an adaptor device;
(b) connect the adaptor device to a reamer;
(c) insert the distal end, the adaptor device and reamer into bony anatomy;
(d) insert a driver into the adaptor device;
(e) rotate the driver to rotate the reamer via the adaptor device;
(f) reposition the robotic arm to re-orient the reamer while the reamer is inserted in the bony anatomy;
(g) stop rotating the driver;
(h) remove the driver from the adaptor device; and
(i) remove the distal end, the adaptor device and the reamer from the bony anatomy.

Another embodiment of the invention relates to a method of performing arthroplasty, the method comprising:
(a) insert a reamer into bony anatomy;
(b) connect a handle having a handle end to an adaptor device, preferably as described herein;
(c) connect the adaptor device to the reamer;
(d) insert a driver into the adaptor device;
(e) rotate the driver to rotate the reamer via the adaptor device;
(f) reposition the handle to re-orient the reamer while the reamer is inserted in the bony anatomy;
(g) stop rotating the driver;
(h) remove the driver from the adaptor device; and
(i) remove the handle end, the adaptor device and the reamer from the bony anatomy.

Another embodiment of the invention relates to a method of performing arthroplasty, the method comprising:
(a) insert a reamer into bony anatomy;
(b) connect a robotic arm having a distal end to an adaptor device;
(c) connect the adaptor device to the reamer;
(d) insert a driver into the adaptor device;
(e) rotate the driver to rotate the reamer via the adaptor device;
(f) reposition the robotic arm to re-orient the reamer while the reamer is inserted in the bony anatomy;
(g) stop rotating the driver;

(h) remove the driver from the adaptor device; and
(i) remove the distal end, the adaptor device and the reamer from the bony anatomy.

Another embodiment of the invention relates to a method of performing arthroplasty, the method comprising:
(a) insert a reamer into bony anatomy;
(b) connect a robotic arm having a distal end to an adaptor device, wherein the distal end comprises a reamer driver adapted to drive the reamer;
(c) connect the adaptor device to the reamer;
(d) rotate the reamer driver to rotate the reamer via the adaptor device;
(e) reposition the robotic arm to re-orient the reamer while the reamer is inserted in the bony anatomy;
(f) stop rotating the reamer driver; and
(g) remove the distal end, the adaptor device and the reamer from the bony anatomy.

Another embodiment of the invention relates to a method of performing arthroplasty, the method comprising:
(a) connect an adaptor device to a reamer
(b) insert a reamer into bony anatomy;
(c) connect a robotic arm having a distal end to the adaptor device, wherein the distal end comprises a reamer driver adapted to drive the reamer;
(d) rotate the reamer driver to rotate the reamer via the adaptor device;
(e) reposition the robotic arm to re-orient the reamer while the reamer is inserted in the bony anatomy;
(f) stop rotating the reamer driver; and
(g) remove the distal end, the adaptor device and the reamer from the bony anatomy.

Another embodiment of the invention relates to a method of performing arthroplasty, the method comprising:
(a) connect an adaptor device to a reamer
(b) connect a robotic arm having a distal end to the adaptor device, wherein the distal end comprises a reamer driver adapted to drive the reamer;
(c) insert a reamer into bony anatomy;
(d) rotate the reamer driver to rotate the reamer via the adaptor device;
(e) reposition the robotic arm to re-orient the reamer while the reamer is inserted in the bony anatomy;
(f) stop rotating the reamer driver; and
(g) remove the distal end, the adaptor device and the reamer from the bony anatomy.

Another embodiment of the invention relates to a method of performing arthroplasty, the method comprising rotating a reamer via an adaptor device as described herein and repositioning the reamer while the reamer is inserted and being rotated in bony anatomy, wherein the adaptor device is connected to a handle or a robotic arm configured to re-orient and direct the reamer.

Related devices, systems, methods of using, assembling and/or operation are also provided and/or described herein and are included in the invention. Other apparatuses, methods, systems, features, and advantages of the devices and systems for using the adaptor devices will be or become apparent to one of ordinary skill in the art upon examination of the following figures and detailed description. It is intended that all such additional apparatuses, methods, systems, features, and advantages be included within this description, be within the scope of the tools, instruments, devices and systems, and be protected by the accompanying claims.

DESCRIPTION OF THE FIGURES

The above-mentioned and other features of the inventions disclosed herein are described below with reference to the drawings of the preferred embodiments. The illustrated embodiments are intended to illustrate, but not to limit the inventions. The drawings contain the following figures:

FIG. 3A is a top side perspective view of the adaptor device. FIG. 3B is a cross-sectional of the adaptor device of FIG. 3A. FIG. 3C is a cross-section view of FIG. 3A along dashed lines B-B' shown in FIG. 3B.

FIG. 6A is a side perspective illustration of an adaptor tool according to another embodiment connected to a reamer inserted in a bony anatomy and an adjacent reamer driver tool. FIG. 6B is a close-up side perspective illustration of the adaptor device connected to the reamer and adjacent the driver tip shown in FIG. 6A. FIG. 6C is a side perspective illustration of FIG. 6A showing the driver tip inserted into and engaged with the adaptor.

FIG. 10 is a side view of a reamer system comprising the robotic arm of FIG. 9 and a second robotic system configured to support an electric driver and a reamer tool.

DESCRIPTION OF THE INVENTION

Figure 1A:
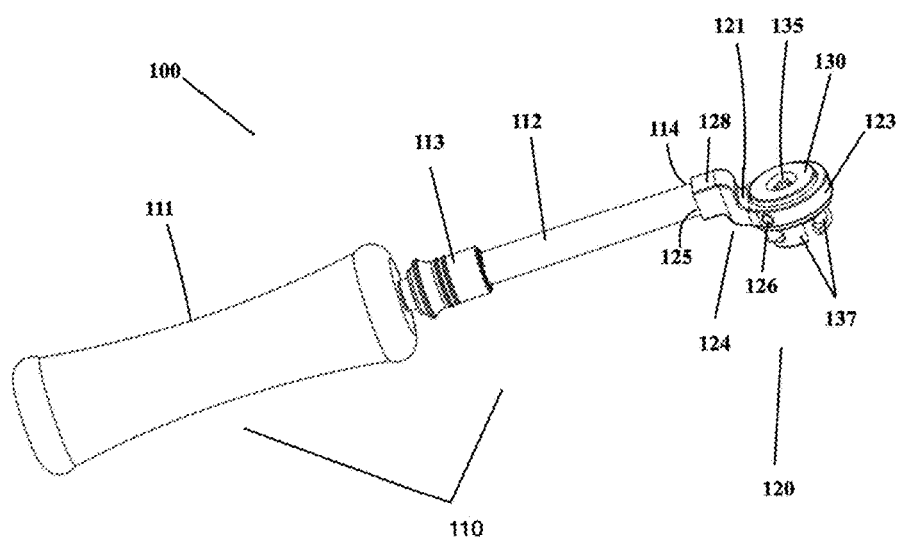
FIG. 1A is an illustration of a side perspective view of an adaptor tool according to one embodiment of the invention.

The present invention can be understood more readily by reference to the following detailed description, examples, and claims, and figures, their previous and following description. In the following description, for purposes of explanation, specific details are set forth in order to provide a thorough understanding of different aspects of the present invention, including the figures. It will be evident, however, to one skilled in the art that the present invention as defined by the claims may include some or all of the features or embodiments herein described and may further include obvious modifications and equivalents of the features and concepts described herein. It is to be understood that this invention is not limited to the specific systems, devices, and/or methods disclosed unless otherwise specified, as such can, of course, vary. It is also to be understood that the terminology used herein is for the purpose of describing particular aspects only and is not intended to be limiting unless included in the claims.

The following description of the invention is provided as an enabling teaching of the invention in its best, currently known aspect. Those skilled in the relevant art will recognize that many changes can be made to the aspects described, while still obtaining the beneficial results of the present invention. It will also be apparent that some of the desired benefits of the present invention can be obtained by selecting some of the features of the present invention without utilizing other features. Accordingly, those who work in the art will recognize that many modifications and adaptations to the present invention are possible and can even be desirable in certain circumstances and are a part of the present invention. Thus, the following description is provided as illustrative of the principles of the present invention and not in limitation thereof.

DEFINITIONS

As used herein, the singular forms "a," "an" and "the" include plural referents unless the context clearly dictates otherwise. Thus, for example, reference to a "pin" or "shaft" or an "connector" includes aspects having two or more such pins, shafts or connectors unless the context clearly indicates otherwise.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect and "about" is utilized herein to represent an inherent degree of uncertainty that may be attributed to any quantitative comparison, value, measurement, or other representation. These terms are also utilized herein to represent the degree by which a quantitative representation may vary from a stated reference without resulting in a change in the basic function of the subject matter at issue. It will be further understood that the endpoints of each of the ranges are significant both in relation to the other endpoint, and independently of the other endpoint.

As used herein, the terms "optional" or "optionally" mean that the subsequently described event or circumstance may or may not occur, and that the description includes instances where the event or circumstance occurs and instances where it does not.

Terms used herein, such as "exemplary" or "exemplified," are not meant to show preference, but rather to explain that the aspect discussed thereafter is merely one example of the aspect presented.

Additionally, as used herein, relative terms, such as "substantially", "generally", "approximately", and the like, are utilized herein to represent an inherent degree of uncertainty that may be attributed to any quantitative comparison, value, measurement, or other representation. These terms are also utilized herein to represent the degree by which a quantitative representation may vary from a stated reference without resulting in a change in the basic function of the subject matter at issue.

The terms "quick connect" or "quick connect/release" refers to Hudson connectors, and similar mechanical adaptors or connection means configured and adapted to easily connect one component to another (and disconnect one from another) without additional equipment or tools and/or release one component from another without additional equipment or tools.

The invention relates to adaptors for use with bone reaming, cutting, abrading, and/or other bone modification systems and methods of using the same. Preferably, the present invention relates to orthopedic surgical reamers and more specifically to adaptor devices and/or drivers for such tools.

More specifically, the invention relates to an adaptor device for a bone cutting system, the adaptor device comprising:
  (a) an adaptor head configured to reversibly connect to a bone cutter and further configured to reversibly engage with a bone cutter driver; and
  (b) an adaptor housing configured to connect to the adaptor head and further configured to attach to a handle for the adaptor device and/or a robotic arm for the adaptor device.

Preferably, the bone cutter is configured for cutting a hemispherical cavity in bone.

According to preferred embodiments of the present invention, there is provided a tool for cutting a hemispherical cavity in bone. The tool is preferably part of a reaming system that utilizes a driver with quick disconnect catches that receive mounting bars on the tool.

One embodiment of the invention relates to an adaptor device for an arthroplasty reaming system, the adaptor device comprising:
  (a) an adaptor head configured to reversibly connect to a reamer and further configured to reversibly engage with a reamer driver; and
  (b) an adaptor housing configured to connect to the adaptor head and further configured to attach to a handle for the adaptor device and/or a robotic arm for the adaptor device.

Figure 1B:
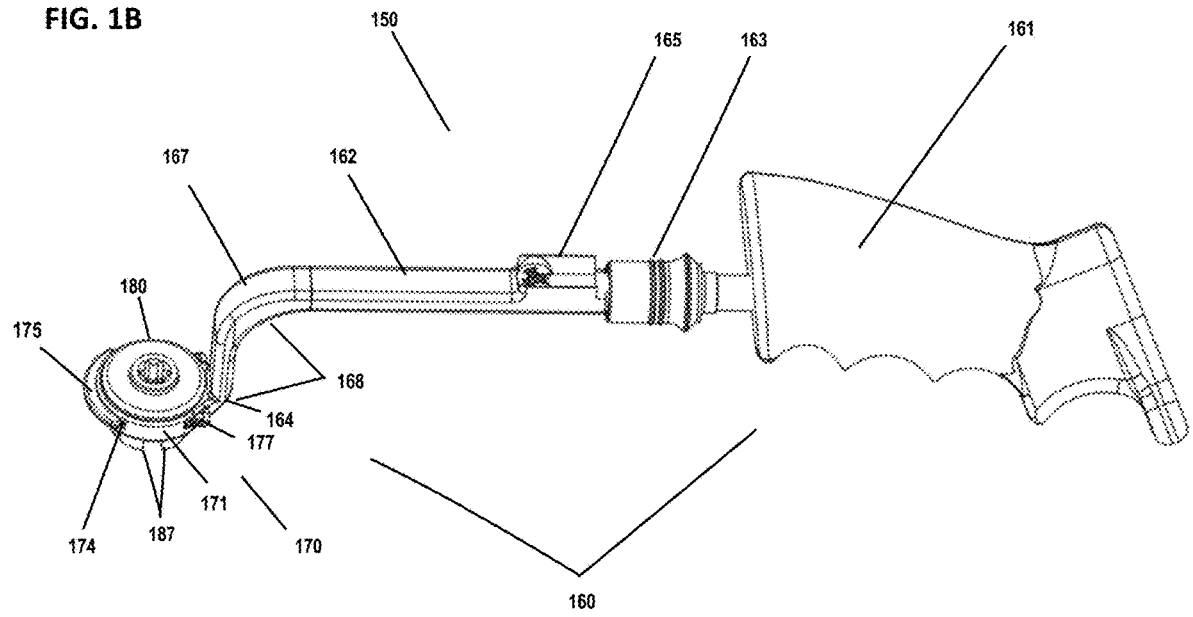
FIG. 1B is a side perspective view of another adaptor tool according to another embodiment of the invention.

Preferably, the adaptor housing comprises a handle adaptor or connector configured to connect to a handle and/or a robotic arm. According to preferred embodiments, the handle adaptor or robotic arm adaptor comprises a recess for receiving a shaft of the handle as shown in FIGS. 1A-B, for example or receiving the distal end of the robotic arm.

Preferably, the adaptor head includes a reamer driver seat configured to engage the reamer driver.

According to preferred embodiments, the adaptor head has a first side comprising one or more structures to engage the reamer and a second side comprising the reamer driver seat. Preferably, the reamer driver seat is a recess adapted to engage the reamer driver. According to one preferred embodiment, the reamer driver seat is configured to connect to a reamer driver connected to a robotic arm.

According to preferred embodiments, the reamer driver comprises a ball nosed tip and, preferably the reamer driver seat is configured to engage the ball nosed tip. Even more preferably, the ball nosed tip is configured to engage the reamer driver seat at variable angles.

Preferably, the adaptor device is configured for independent orientation of the reamer relative to the reamer driver. For example, the adaptor device is configured to change the orientation of the reamer relative to the reamer driver, preferably, while the reaming process is occurring. Alternatively, the reaming process is paused before each change in orientation of the reamer. Preferably, the adaptor device is configured for independent orientation of the reamer relative to the bony anatomy as well, preferably during rotation of the reamer.

Preferably, the adaptor device further comprises a handle connected to the adaptor housing. According to preferred embodiments, the handle comprises a grip and a shaft and the shaft is connected to the adaptor housing. Preferably, the grip is connected to the shaft using a quick connect, as shown in FIGS. 1A-B, for example.

According to alternative preferred embodiments, the adaptor device is configured to connect to a robotic arm. Preferably, the robotic arm has a distal end configured to connect to the adaptor housing and/or configured to connect to a shaft configured to connect to the adaptor housing. According to one preferred alternative embodiment, the robotic arm is connected to the adaptor housing via a quick connect, as shown as quick connect 113 in FIG. 1A or via a connection as shown as the distal end 305 connected via connector 303 in FIG. 3A, for example.

Preferably, the adaptor housing comprises a ring-like or annular structure to hold the adaptor head and the adaptor head can freely rotate within the ring-like or annular structure while being held.

Preferably, the adaptor housing connects to the adaptor head using a quick release connection (e.g., pins around the circumference of the adaptor housing which hold the adaptor head and can be pressed to release the adaptor head from the adaptor housing).

Preferably, the adaptor head comprises a first side comprising one or more structures to engage the reamer. According to preferred embodiments, the one or more structures are configured to mate with different types of reamers. Preferably, the one or more structures are configured to snap into place onto the reamer. Preferably, the one or more structures are configured to rotate into place to engage the reamer.

FIG. 1A shows an adaptor tool 100 according to one embodiment of the invention configured to connect to a reamer (not shown) comprising a handle 110 for positioning and manipulating the reamer and including a handle grip 111 and a handle shaft 112 and a quick connect connector 113 connecting the grip 111 to the shaft 112.

According to preferred embodiments, handle 110 has a length between 0.5 inch and 24 inches, more preferably between 4 inches and 12 inches.

Shaft 112 includes a distal end 114 connected to adaptor device 120 comprising an adaptor housing 121 and adaptor head 130. Adapter housing 121 comprises an annular ring 123 and connector 124 for connecting to the distal end 114 of shaft 112. Annular ring 123 holds adaptor head 130. Adaptor head 130 is configured to connect to a reamer or other cutting tool using structures 137.

According to alternative embodiments, annular ring 123 can be replaced with a C-shaped structure to hold the adaptor head 130 or other gripping structure to hold the adaptor head 130 while allowing it to freely rotate (e.g., comprised of three or more gripping structures around the outer circumference of the adaptor head to support while allowing the adaptor head to freely rotate). An annular ring surrounding the adaptor head is preferred.

Preferably, adaptor head 130 snaps into annular ring 123 and, more preferably, can be released using release pin 126.

Connector 124 preferably comprises a recess 125 for receiving distal end 114 of shaft 112. As shown in FIG. 1A, recess 125 is at the end of a connector support structure 128. The connector support structure 128 shown in FIG. 1A allows the central axis of the handle 110 to be displaced relative to the top surface of the adaptor housing 121 to allow or provide the handle 110 with an increased range of motion when the adaptor housing 121 is embedded in tissue while accessing the location of the bony anatomy being modified.

According to alternative embodiments, recess 125 is within the side of annular ring 123 allowing the distal end 114 to be attached to the side of annular ring 123. Preferably, according to these alternative embodiments, all or a portion of the outer surface of annular ring 123 is tapered to allow the handle 110 to be connected to the annular ring 123 at an angle.

Annular ring 123 is configured to hold adaptor head 130 while adaptor head 130 is free to rotate within annular ring 123 and thus rotate relative to handle 110. As also shown in FIG. 1A, adaptor head 130 includes a top side having a driver tip recess 135 configured for receipt of the reamer driver tip (not shown) and a bottom side comprising one or more structures 137 to engage the reamer (not shown).

According to alternative embodiments, adaptor housing 121, for example including annular ring 123 or similar gripping or holding structure, is configured to connect directly to the reamer or other cutting device, while allowing the reamer or other cutting device to freely rotate (e.g., adaptor head 130 omitted). According to one embodiment, the reamer or other cutting device comprising a cutting side and an opposing side and the opposing side comprises a driver tip recess configured for receipt of the reamer driver tip.

FIG. 1B shows an alternative adaptor tool 150 according to another embodiment of the invention configured to connect to a reamer (not shown) comprising a handle 160 for positioning and manipulating the reamer and including a "Pistol Grip" handle 161 and a handle shaft 162 and a quick connect connector 163 connecting "Pistol Grip" handle 161 to the shaft 162. Shaft 162 includes a distal end 164 connected to adaptor device 170 comprising an adaptor housing 171 and adaptor head 180.

As shown in FIG. 1B, distal end 164 is offset from shaft 162 by shaft elbow 167 allowing an alternative offset orientation of the adaptor handle 160 relative to the reamer. The additional offset distance 168 shown provides a further increased range of motion (compared to FIG. 1A) when the adaptor housing 171 is embedded in tissue while accessing the location of the bony anatomy being modified. The offset distance 168 can vary depending on the offset requirements. According to preferred embodiments, the offset distance 168 (determined by the distance between the plane of the bottom of the shaft 162 and the plane of the top of the adaptor housing 171) ranges from 0.5 inch to 8 inches, preferably 1 inch to six inches.

Figure 5A:
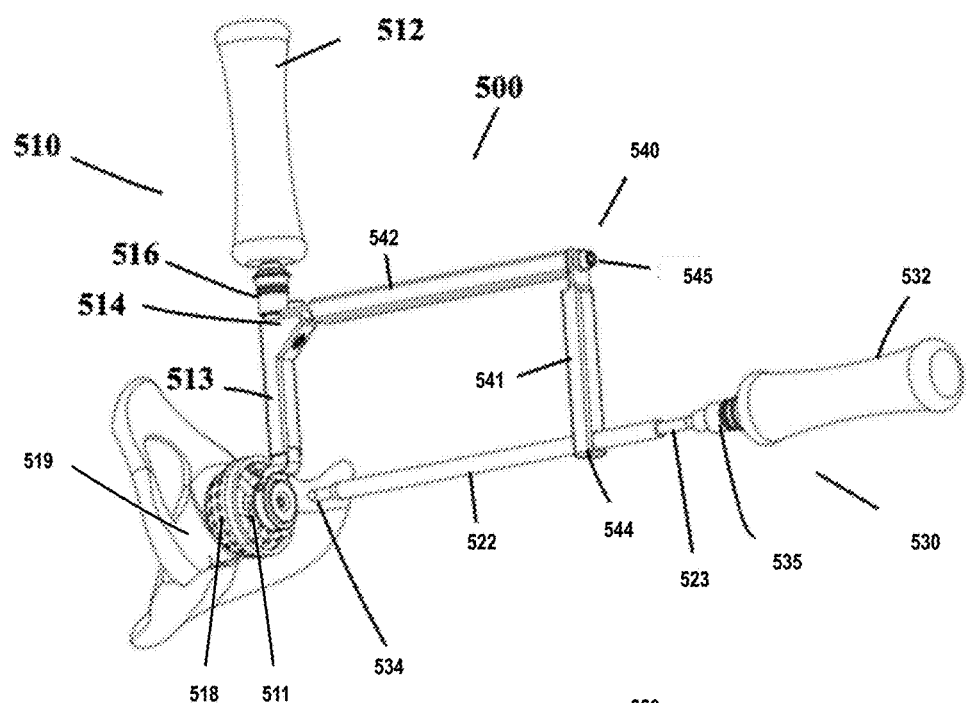
FIG. 5A is a side perspective illustration of an adaptor tool including a guide arm according to another embodiment connected to a reamer inserted into a bony anatomy.
Figure 5B:
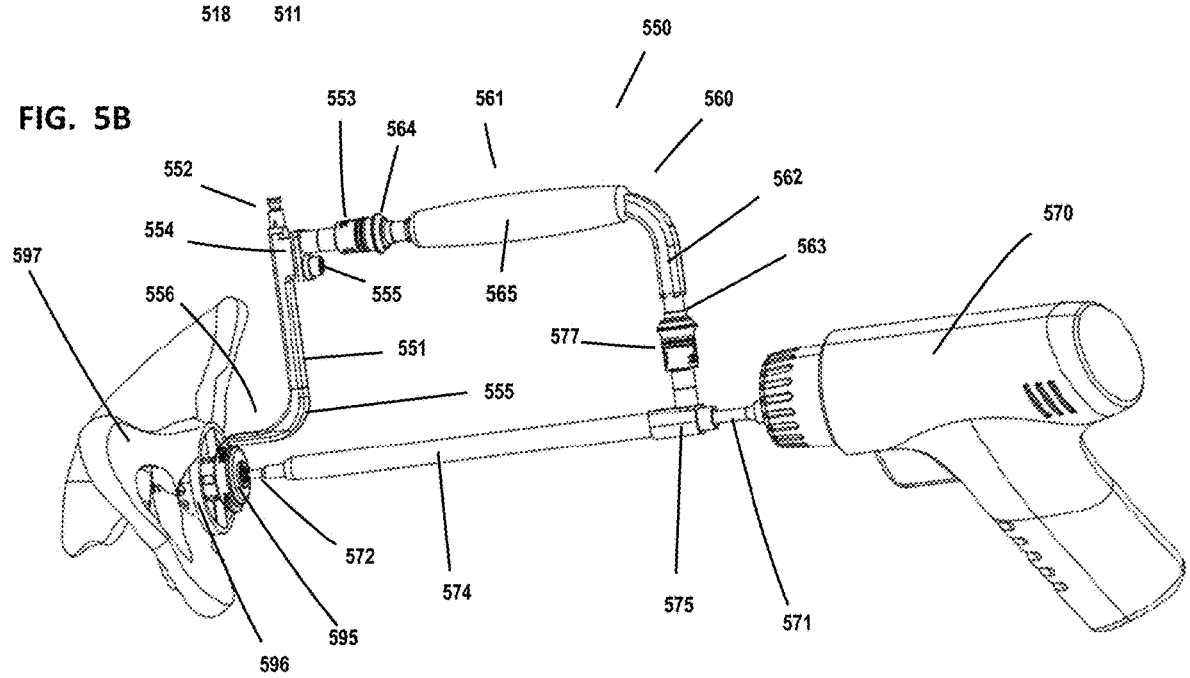
FIG. 5B is a side perspective illustration of another adaptor tool including an alternative guide arm according to yet another embodiment connected to a reamer inserted into a bony anatomy.

As shown in FIG. 1B, shaft 162 comprises connector 165 configured to connect the shaft 162 to a guide support or targeting arm (not shown) as shown in FIGS. 5A and 5B. According to one embodiment, connector 165 is a V-grooved slot configured to allow the end of a targeting arm to be threaded onto the connector 165 and secured with a bolt, for example. According to another embodiment, connector 165 is a quick connect connector (e.g., like connector 163).

Figure 8A:
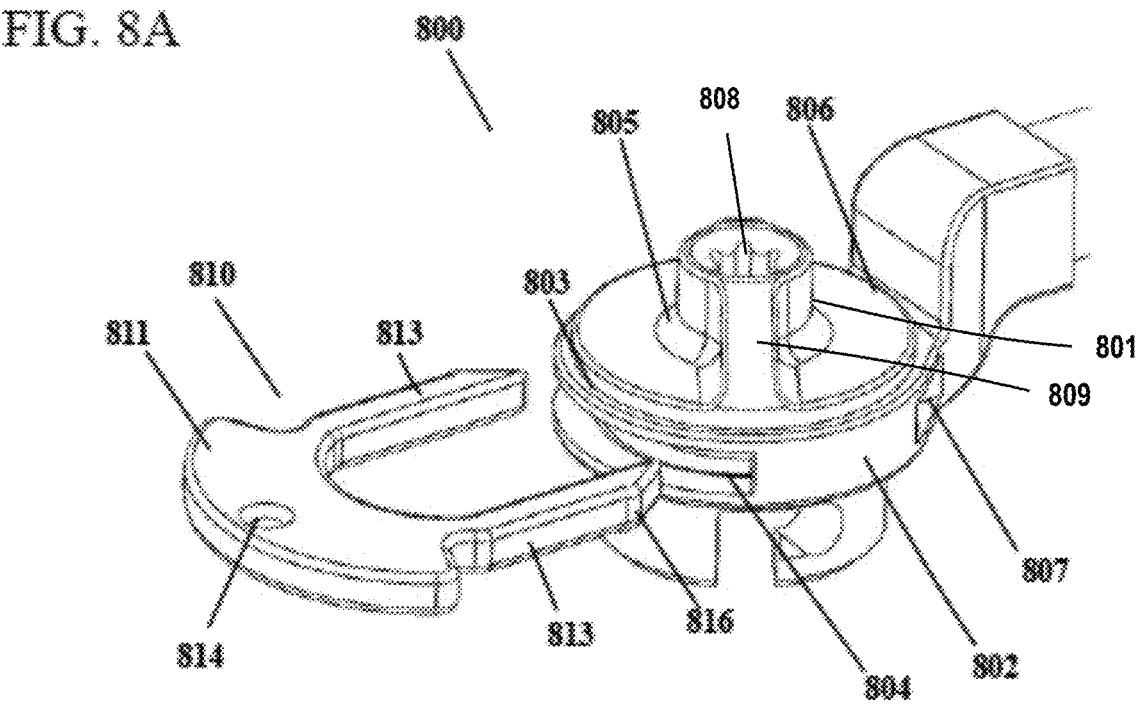
FIG. 8A-B show an adaptor device according to another preferred embodiment showing an adaptor head secured within an adaptor housing using a clip.
Figure 8B:
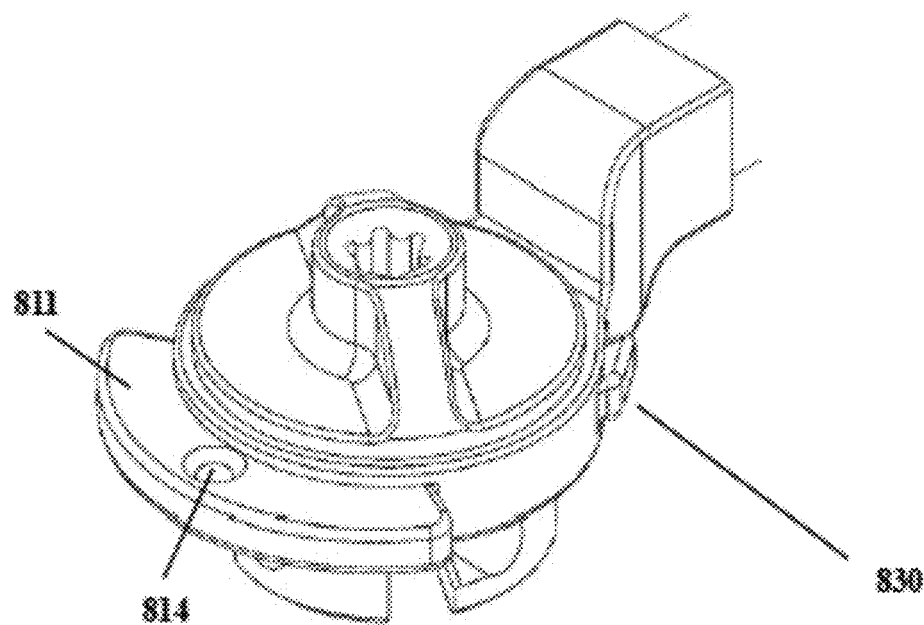

Adapter housing 171 includes a clip recess 174 for receipt of clip 175 and an opposing side of adaptor housing 171 including one or more rear recesses 177. Clip 175 is preferably configured to be assembled into adaptor housing 171 as shown in FIG. 1B to lock the adaptor head 180 in place while allowing the adaptor head 180 to freely rotate within adaptor housing 171, similar to as shown in FIGS. 8A-B (discussed below). Adaptor head 180 is configured to connect to a reamer or other cutting tool (not shown) using structures 187.

Another embodiment of the invention relates to an adaptor device for an arthroplasty reaming system, the adaptor device comprising an adaptor configured to reversibly connect to a reamer and further configured to reversibly engage with a reamer driver, wherein the adaptor is still further configured to connect to a handle and/or robotic arm and configured to allow the reamer orientation to be varied relative to the reamer driver using the handle and/or robotic arm.

Another embodiment of the invention relates to an adaptor device for an arthroplasty reaming system, the adaptor device comprising an adaptor means configured to reversibly connect to a reamer means and further configured to reversibly engage with a reamer driver means, wherein the adaptor means is still further configured to connect to a handle means and/or a robotic arm and configured to allow the reamer orientation to be varied relative to the reamer driver means using the handle and/or robotic arm.

Another embodiment of the invention relates to an arthroplasty reaming system comprising one or more of the adaptor devices described herein and a reamer driver.

Preferably, the reamer driver comprises a distal end having a ball nosed driver tip. According to preferred embodiments, the adaptor device comprises a recess configured to engage the ball nosed driver tip.

Preferably, the adaptor device is configured to provide independent control of the reamer orientation. According to preferred embodiments, the independent control of the reamer orientation allows the reamer driver to be out of line from reaming direction.

Preferably, the system further comprises a reamer connected to the adaptor head of the adaptor device.

Figure 2A:
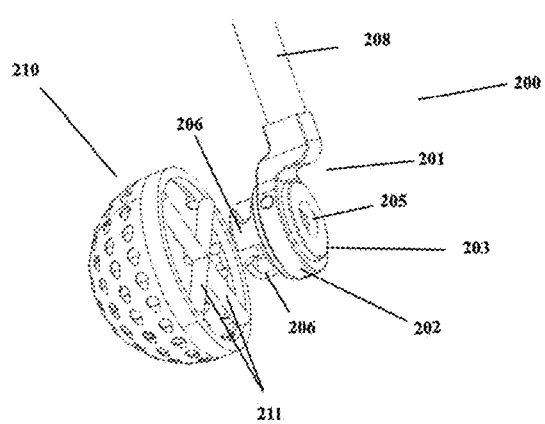
FIGS. 2A-D are side perspective illustrations of adaptor devices according to preferred embodiments configured to connect to reamers having different interface configurations.
Figure 2B:
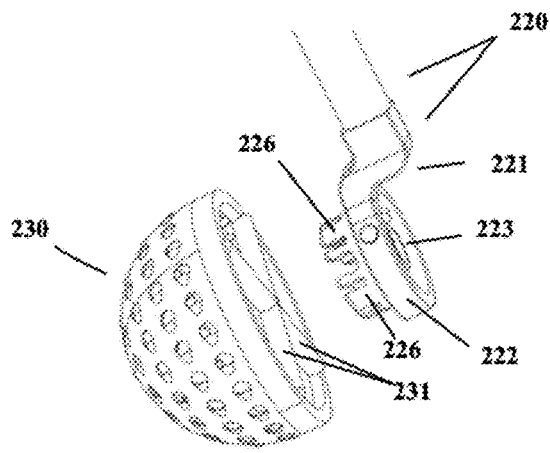
Figure 2C:
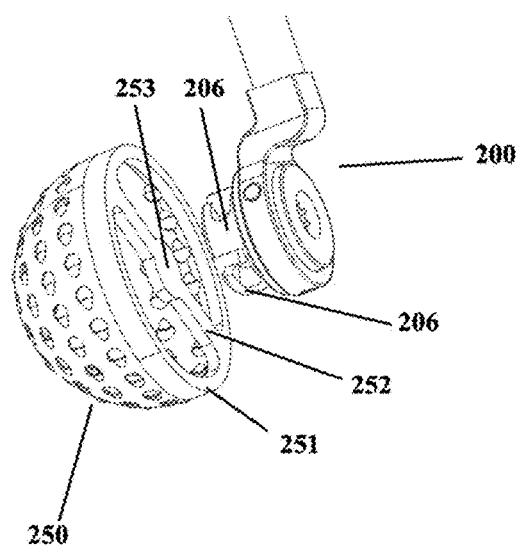

FIGS. 2A-C show the adaptor configurations to mate with different reamer types (crossing round bars or flat single bar) where the interface between the adaptor head and reamer may rotate into place or snap into place.

FIG. 2A shows an adaptor tool 200 including an adaptor device 201 adjacent reamer 210. Adaptor device 201 comprises adaptor annular housing 202 holding adaptor head 203 allowing adaptor head 203 to freely rotate within housing 202. Adaptor device 201 is connected to shaft 208 of handle (not shown). Adaptor head 203 comprises a top side comprising driver tip recess 205 and a bottom side comprising one or more adaptor structures 206 configured to engage corresponding reamer interface structures 211 to connect (preferably reversibly connect) the adaptor head 203 to reamer 210.

As shown in FIG. 2A, the one or more adaptor structures 206 are configured to be inserted and rotated to lock in place with corresponding reamer interface structures 211. According to the embodiment shown in FIG. 2A, reamer interface structures 211 are configured as crossing bars (forming an X configuration) configured to allow each adaptor structure 206 to engage and lock onto each corresponding crossing bar segment.

FIG. 2B shows an adaptor tool 220 including an adaptor device 221 adjacent reamer 230. Adaptor device 221 comprises adaptor annular housing 222 holding adaptor head 223 allowing adaptor head 223 to rotate within adaptor annular housing 222. FIG. 2B shows alternative adaptor structures 226 configured to snap onto the corresponding reamer interface structures 231.

FIG. 2C shows the adaptor tool 200 of FIG. 2A adjacent reamer 250 having an interface structure 251 comprising a flat single bar 252 having an enlarged or expanded center portion 253. As shown in FIG. 2C, adaptor structures 206 are configured to engage and lock onto bar 252.

Figure 2D:
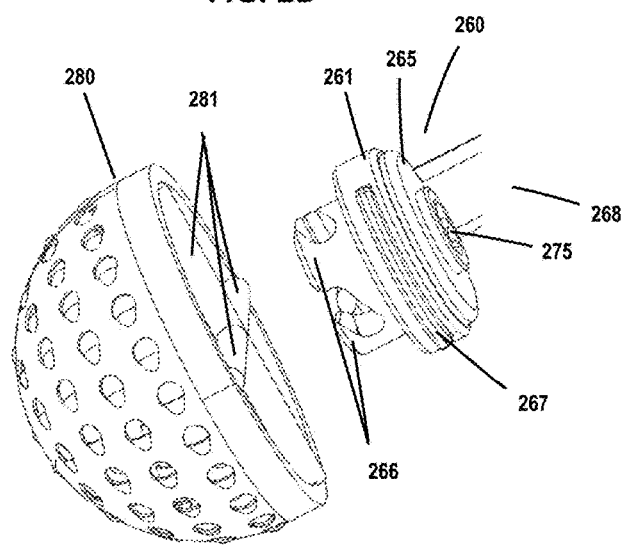

FIG. 2D shows an alternative adaptor tool 260 adjacent reamer 280. Adaptor tool 260 comprises adaptor housing 261 holding adaptor head 265 allowing adaptor head 265 to freely rotate within adaptor housing 261. Adaptor device 260 is connected to shaft 268 of handle (not shown).

Adaptor head 265 comprises a top side comprising driver tip recess 275 and a bottom side comprising one or more adaptor structures 266 configured to engage corresponding reamer interface structures 281 to connect (preferably reversibly connect) the adaptor head 265 to reamer 280. Adaptor housing 261 includes clip recess 267 for receipt of locking clip (not shown).

As shown in FIG. 2D, adaptor structures 266 have a spiral pattern to mate with reamer interface structures 281 of reamer 280. The spiral pattern of structures 266 allow the adaptor to engage with the reamer when turned clockwise and disengage when turned counterclockwise. Reamer 280 comprises reamer interface structures 281 configured as rounded crossing bars (forming an X configuration) configured to allow each adaptor structure 266 to engage and lock onto each corresponding crossing bar segment. Preferably, the spiral pattern of structures 266 are configured so that the adaptor moves closer to, and preferably more securely tightens onto, the corresponding reamer interface structures 281 of reamer 280 when the structures 266 are turned to engage the reamer, while does the opposite when turned to disengage (e.g., like the lid of a jar when screwed onto the jar and when screwed off to remove the lid).

Figure 3A:
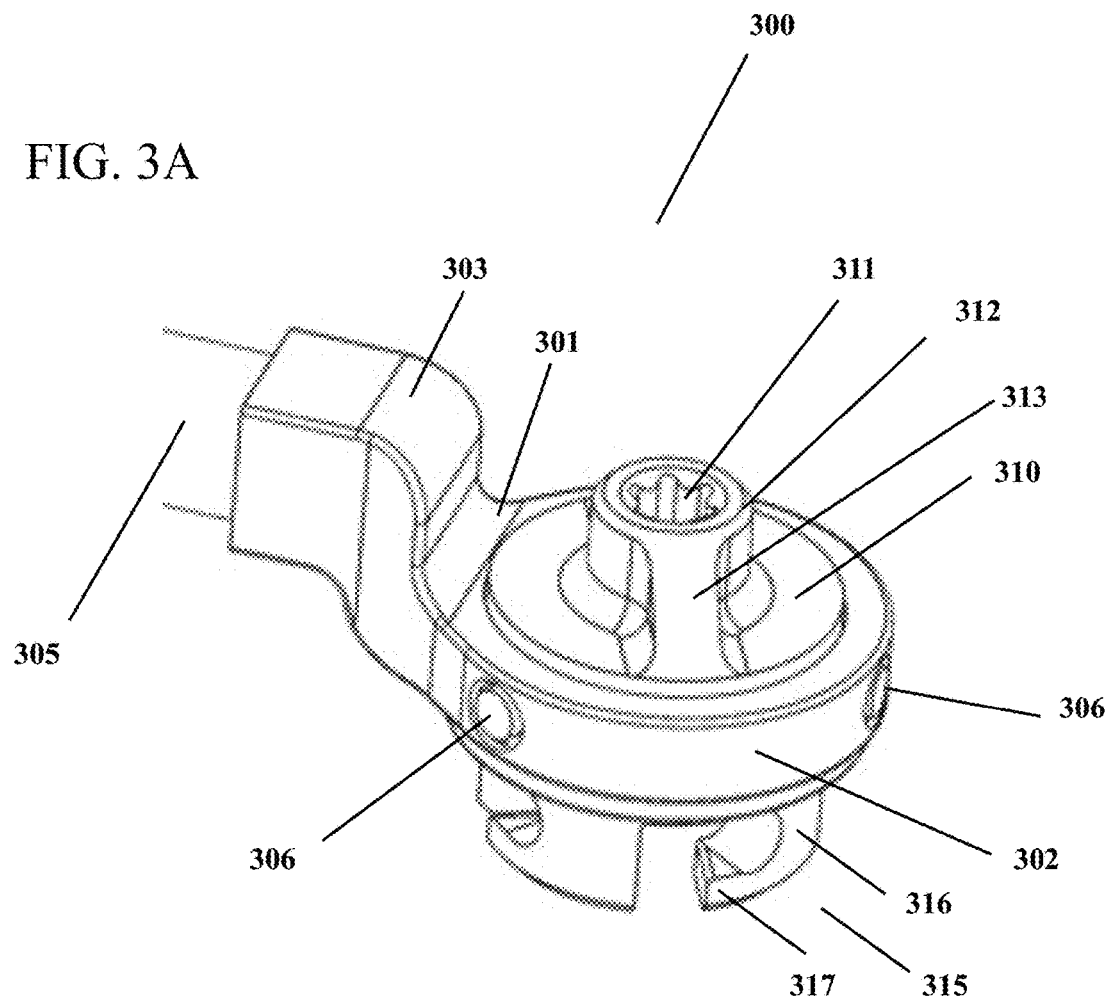
FIGS. 3A-C show the adaptor device according to one preferred embodiment showing an adaptor head within an adaptor housing.
Figure 3B:
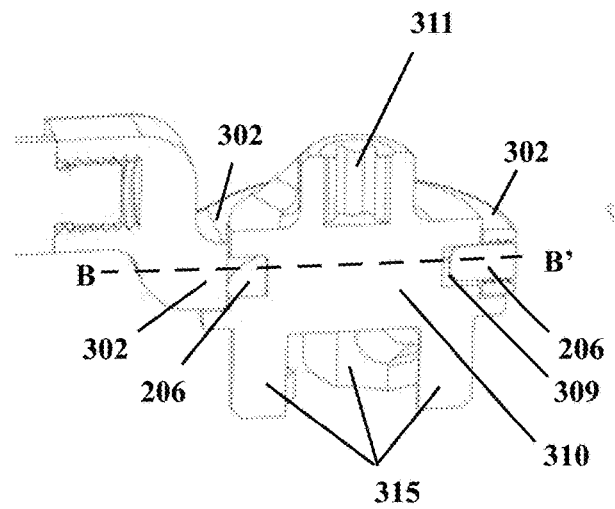
Figure 3C:
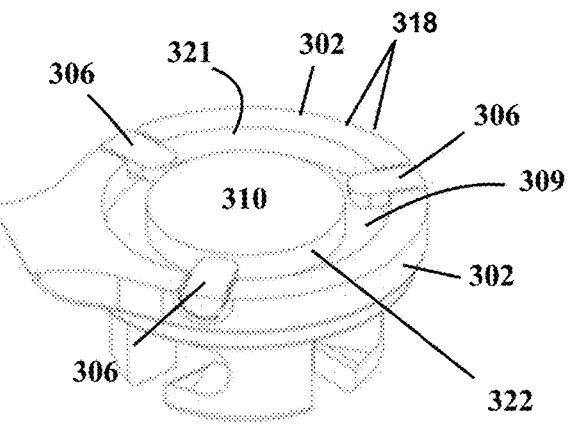

FIGS. 3A-C show the adaptor device 300 according to another embodiment showing adaptor housing 301 including annular ring 302 surrounding adaptor head 310. Adaptor housing 301 comprises connector 303 to connect to distal end 305 of handle (not shown). Adaptor head 310 has a top side comprising a driver recess 311 configured for engaging a reamer driver tip (not shown) and a bottom side comprising one or more adaptor structures 315 configured to engage and reversibly lock onto the reamer interface (not shown). Driver recess 311 as shown is enclosed in a raised center 312 on the top surface of the adaptor head 310 and the raised center 312 includes a flange 313 to facilitate turning or otherwise adjusting the adaptor head 310 with a hand, pliers or similar tool (e.g., allows a tool or hand to grip to spin and lock onto the reamer).

Annular ring 302 includes release/locking pins 306 to depress to release the adaptor head 310 from the adaptor housing 301 and/or snap the adaptor head 310 into the adaptor housing 301, while allowing the adaptor head 310 to freely rotate within annular ring 302 (e.g., when rotated by a reamer driver). Preferably, the annular ring 302 comprises at least two (2) pins, preferably at least three (3) pins, and most preferably at least four (4) pins 306 around the outer circumference of the annular ring 302.

The one or more adaptor structures 315 are L-shaped and comprise a vertical leg 316 connected or integral to the bottom of adaptor head 310 and horizontal foot 317 attached or integral with the vertical leg 316 and configured to reversibly engage and lock onto the interface of the reamer (not shown) by insertion and rotation.

FIG. 3B is a cross-sectional view of the adaptor device 300 of FIG. 3A. FIG. 3B shows the cross-section of adaptor head 310 including the top side including recess 311 configured to engage reamer driver tip (not shown) and the bottom side comprising adaptor structures 315. Adaptor head 310 is held within annular ring 302 and allowed to freely rotate. Adaptor head 310 can be locked and released from annular ring 302 using pins 306 (e.g., depressing the pins).

FIG. 3C is a cross-section view of FIG. 3A along lines B-B' shown in FIG. 3B. As shown in FIG. 3C, according to preferred embodiments, there is an annular gap 309 between the inner surface 321 of annular ring 302 and outer surface 322 of the portion of adaptor head 310 held within the annular ring 302 to ensure free rotation of adaptor head 310. Preferably, the annular gap 309 ranges from 0.1 mm to 0.5 cm.

Annular ring 302 preferably has a width 318 ranging from 0.5 cm to 5 cm.

FIGS. 8A and 8B show adaptor device 800 as an alternative to using the pins 126 or 306 shown in FIGS. 1-3. Specifically, FIG. 8A shows adaptor housing 802 having a distal side 803 comprising a clip recess 804 for receipt of clip 810 and an opposing side 806 including one or more rear recesses 807.

Clip 810 is preferably configured to be assembled into adaptor housing 802 as shown in FIG. 8B to lock the adaptor head 805 in place while allowing the adaptor head 805 to freely rotate within adaptor housing 802. Preferably, the clip 810 is configured to allow the rotation/load bearing on the top and bottom sides of clip 810.

As shown in FIG. 8A, according to preferred embodiments, clip 810 is C-shaped or horseshoe-shaped and includes a grip 811 to facilitate insertion (and removal) of prongs 813 into clip recess 804 of adaptor housing 802.

Preferably, grip 811 includes at least one hole or indent 814 to facilitate insertion and removal with a tool or instrument.

As shown in FIG. 8A, the distal end of each prong 813 may include a locking structure 816 to catch and reversibly lock 830 when inserted through clip recess 804 and through rear recess 807. Preferably, the distance between the distal end of each prong 813 narrows when clip 810 is initially inserted into clip recess 804 but then expands to catch 830 the edge of rear recess 807 when passes through rear recess 807. Clip 810 can then be removed by pulling on grip 811, and if needed, pressing on locking structure 816 to push out of rear recess 807.

As shown in FIG. 8A-B, driver recess 808 is enclosed in a raised center 801 on the top surface of the adaptor head 805 and the raised center 801 includes a flange 809 to facilitate turning or otherwise adjusting the adaptor head 805 with a hand, pliers or similar tool (e.g., allows a tool or hand to grip to spin and lock onto the reamer, not shown).

Figure 8C:
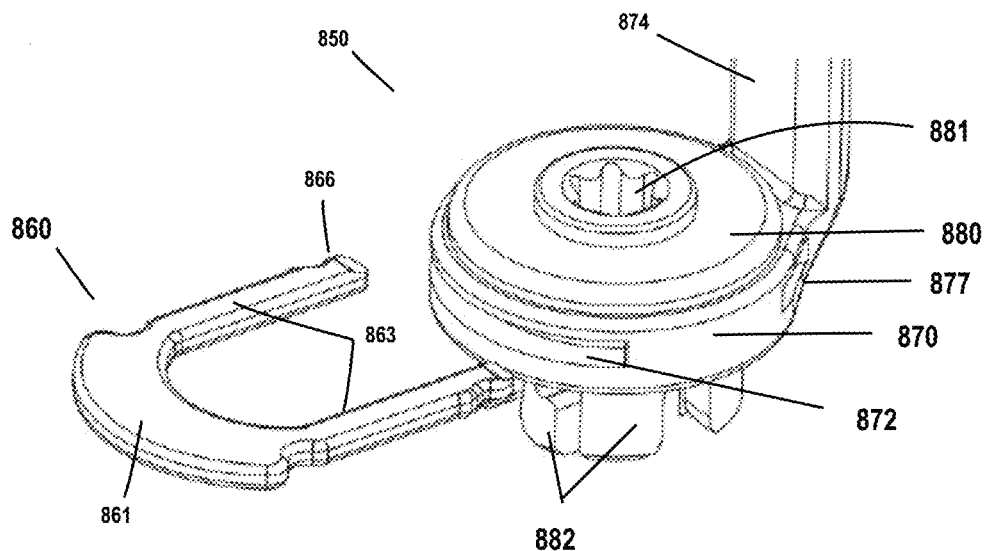
FIG. 8C-D show an adaptor device according to yet another preferred embodiment showing an adaptor head secured within an adaptor housing using a clip.
Figure 8D:
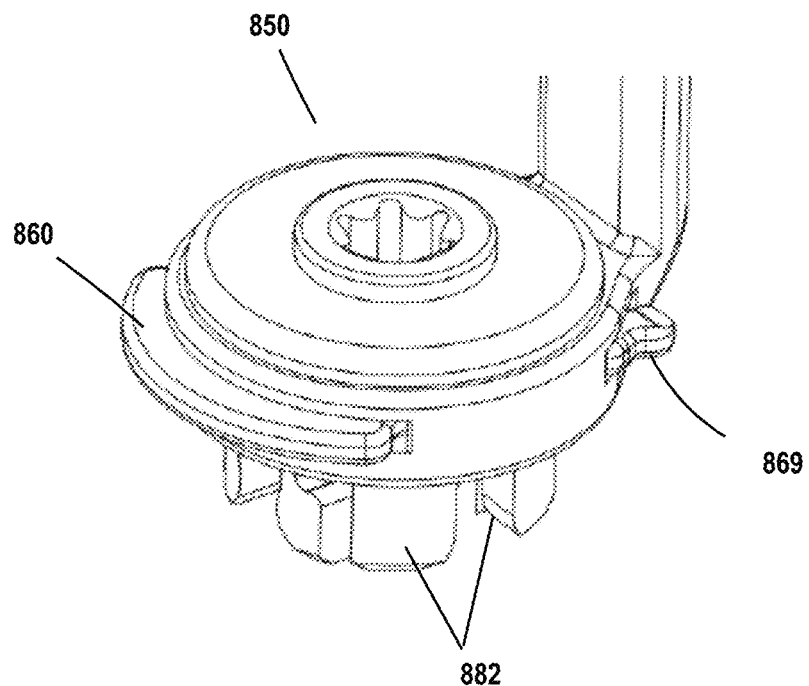

FIGS. 8C and 8D show adaptor device 850 according to an alternative embodiment comprising adaptor housing 870 connected to shaft or shaft connector 874 and holding adaptor head 880.

Shaft or shaft connector 874 is configured to provide a larger offset of the adaptor device 850 relative to the handle or robotic arm (not shown) providing increased range of motion when the adaptor device 850 is embedded in tissue while accessing the location of the bony anatomy being modified.

FIG. 8C also shows adaptor housing 870 comprising a clip recess 872 on a first side for receipt of clip 860 and an opposing side including one or more rear recesses 877. Clip 860 is preferably configured to be assembled or inserted into adaptor housing 870 as shown in FIG. 8D to lock the adaptor head 880 in place while allowing the adaptor head 880 to freely rotate within adaptor housing 870. Preferably, the clip 860 is configured to allow the rotation/load bearing on the top and bottom sides of clip 860.

As shown in FIG. 8C, according to preferred embodiments, clip 860 is C-shaped or horseshoe-shaped and includes a grip 861 to facilitate insertion (and removal) of prongs 863 into clip recess 872 of adaptor housing 870. As shown in FIG. 8C, the distal end of each prong 863 may include a locking structure 866 to catch and reversibly lock when inserted through clip recess 872 and through rear recesses 877. Preferably, the distance between the distal end of each prong 863 narrows when clip 860 is initially inserted into clip recess 872 but then expands to catch 869 the edge of each rear recess 877 when passes through rear recesses 877. Clip 860 can then be removed by pulling on grip 861, and if needed, pressing on locking structures 866 to push out of rear recess 877.

As also shown in FIGS. 8C and 8D, adaptor head 880 comprises adaptor structures 282 having a spiral pattern to mate with reamer interface structures of reamer (not shown).

As also shown in FIGS. 8C-D, adaptor head 880 has a lower profile compared to adaptor head 805 having raised center 801 of FIG. 8A. Preferably, the lower profile and/or an increased offset is configured to help facilitate introduction of the adaptor head 880 connected to reamer (not shown) into the incision.

According to preferred embodiments, a portion of the outer circumference of the adaptor head and/or interior surface of the annular ring comprises a coating or insert to reduce any friction (e.g., Teflon) between the adaptor head and housing during rotation.

As discussed above, according to alternative embodiments, adaptor housing connects directly to the reamer or cutting device and preferably a portion of the outer circumference of the reamer/cutting device and/or interior surface of the annular ring comprises a coating or insert to reduce any friction (e.g., Teflon) between the reamer/cutting device and adaptor housing during rotation Reamers/adaptor heads according to the invention can have a wide variety of locking interfaces to lock the adaptor head (or adaptor housing) onto the reamer such as the interface structures shown in U.S. Pat. No. 5,658,290 to Lechot (e.g., FIGS. 1-2); U.S. Pat. No. 6,854,742 to Salyer et al. (e.g., FIGS. 1 and 10); U.S. Pat. No. 7,115,119 to Desarzens (e.g., FIG. 1); U.S. Pat. No. 7,993,348 to Conte et al. (e.g., FIG. 7); and U.S. Pat. No. 9,173,663 to Ryall et al. (e.g., FIGS. 1-4), each hereby incorporated by reference. The invention broadly relates to adaptor housings configured to hold any reamer adaptor while allowing the reamer to freely rotate and the adaptor housing connected to a handle and/or robotic arm to allow the reaming direction to be changed relative to the reamer driver. For example, according to alternative embodiments, the adaptor housing is configured to hold a third party adaptor head while also connected to a handle and also allowing the third party adaptor head to freely rotate within the adaptor housing while being held, for example, as shown in the FIGS. 1-7.

Figure 4A:
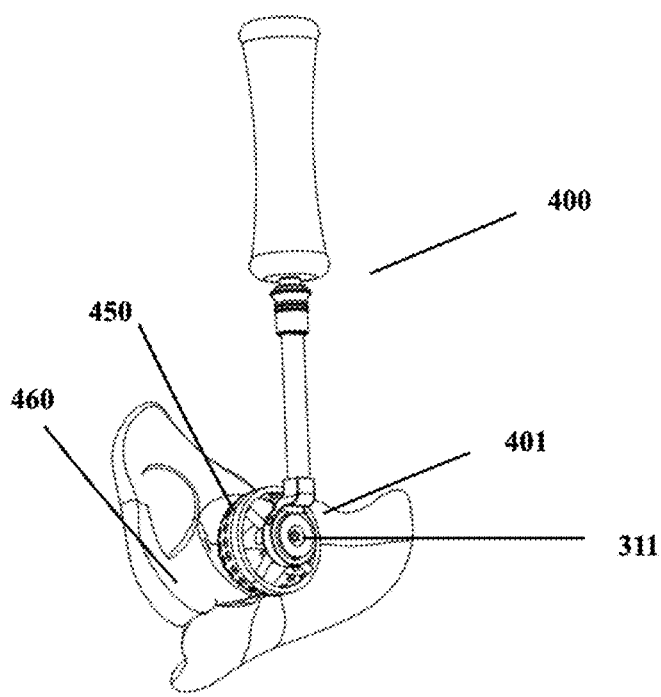
FIG. 4A is a side perspective illustration of an adaptor tool according to another embodiment connected to a reamer inserted into bony anatomy.

FIG. 4A shows an adaptor tool 400 including an adaptor device 401 according to another embodiment of the invention engaged with reamer 450 and dropped into position in the acetabulum/glenoid bony anatomy 460. Recess 311 is configured to engage with reamer driver (not shown) is shown on top side of adaptor device 401. For example, in FIG. 5, recess 311 is a female recess with a Phillips-head, Robertson-head or hex-shape configured for the corresponding shaped male tip of the reamer driver tip.

Figure 4B:
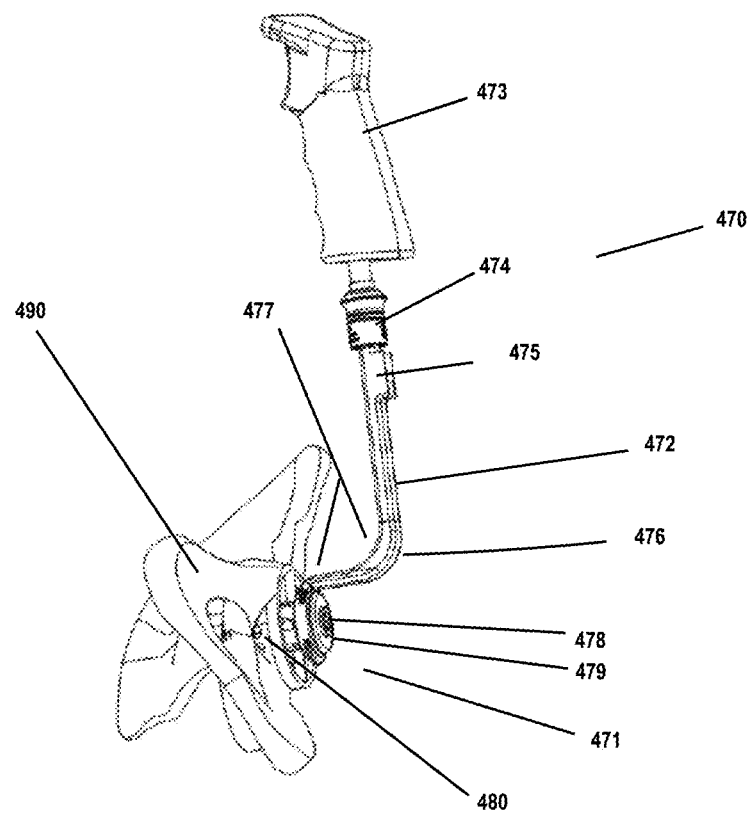
FIG. 4B is a side perspective illustration of another adaptor tool according to yet another embodiment connected to a reamer inserted into bony anatomy.

FIG. 4B shows an adaptor tool 470 including an adaptor device 471 according to another embodiment of the invention engaged with reamer 480 and dropped into position in the acetabulum/glenoid bony anatomy 490. Adaptor tool 470 comprises a shaft 472 connected to grip handle 473 via a quick connect connector 474. Shaft 472 further includes connector 475 configured to connect to a guide support or targeting arm (not shown). As shown in FIG. 4B, shaft 472 includes shaft elbow 476 providing offset portion 477 to offset shaft 472 from adaptor device 471 and reamer 480 providing an increased range of motion when the adaptor device 471 is embedded in tissue while accessing the location of the bony anatomy being modified. Recess 478 is configured to engage with reamer driver (not shown) is shown on top side of adaptor head 479.

Another embodiment of the invention relates to an arthroplasty reaming system comprising one or more adaptor devices as described herein, a reamer driver and a guide arm connected to the handle and reamer driver.

Another embodiment of the invention relates to an arthroplasty reaming system comprising one or more adaptor devices as described herein, a reamer driver and a guide arm connected to a robotic arm and reamer driver.

Preferably, the guide arm is configured to line up the reamer driver or a cannula for use with the reamer driver. Preferably, the guide arm has an L-shape.

Another embodiment of the invention relates to an arthroplasty reaming system comprising one or more adaptor devices as described herein, a cannula for a reamer driver and a guide arm connected to the handle (or robotic arm) and reamer driver and/or cannula. One preferred embodiment is shown in FIG. 5.

FIG. 5A shows an adaptor tool 500 comprising a guide arm 540 connected to the adaptor handle 510 (comprising handle grip 512 and shaft 513) and configured to hold and line-up a cannula 522 for use with the driver shaft 523 of driver 530. FIG. 5A shows a trocar tip 534 configured to use to insert the cannula through tissue of the patient if necessary or preferred by the user. Driver 530 includes driver handle 532 connected to driver shaft 523 via connector 535.

Guide arm 540 is preferably L-shaped and comprises a cannular support 541 connected to a guide support 542, where the connection preferably allows the cannular support 541 to rotate relative to the length of the guide support 542 and more preferably to be disconnected (i.e., the cannular support 541 reversibly connected to a guide support 542). Guide support 542 is connected (preferably reversibly connected) to cannular support 541. Cannular support 541 comprises a first end 544 including a pass-through opening for receipt of cannula 522 as shown in FIG. 5A and second end 545 connected (preferably reversibly connected) to guide support 542. Guide support 542 is connected (preferably reversibly connected) to adaptor handle 510 at connector 514. As shown in FIG. 5A, guide arm 540 holds in place and aligns the cannula 522 for use with the driver shaft 523. As also shown, preferably, guide arm 540 is configured to be removed from the adaptor tool and later re-connected without having to disconnect the adaptor device 511 from the reamer 518. According to preferred embodiments, the guide support 542 is attached between the handle shaft 513 and connector 516.

Preferably, as shown in FIG. 5, guide arm 540 is configured to be connected to the adaptor handle 510 and the cannula 522 and/or driver shaft 523 to enable the entire assembly of the adaptor handle 510 (including adaptor housing) and guide arm 540 to be rotated around the axis of the driver shaft 523 and/or around the adaptor head 511/reamer 518 while inserted into bony anatomy 519. Advantageously, this allows the user (not shown) to adjust the position of the handle without changing the direction of the axis of the driver shaft 523.

FIG. 5B shows an adaptor tool 550 comprising a guide arm 560 connected to the adaptor shaft 551 and configured to hold and line-up a cannula 574 for use with driver shaft 571 of power hand drill 570. FIG. 5B shows a Phillips driver tip 572 inserted into recess of adaptor head 595. Adaptor head 595 is connected to reamer 596 which is inserted into bony anatomy 597.

Guide arm 560 is preferably L-shaped and comprises a cannular support portion 562 and a guide support portion 561. Cannular support portion 562 comprises a first end 563 configured to connect (preferably reversibly connect) to cannula 574, preferably via connector 577 as shown in FIG. 5B. Guide support portion 561 comprises an opposing end 564 connected (preferably reversibly connected) to adaptor shaft 551 via connector 553. Preferably, connector 553 is reversibly connected to adaptor shaft 551 by threading onto the connector 554 and secured with a bolt 555, for example.

As shown in FIG. 5B, guide arm 560 holds in place and aligns the cannula 574 for use with the driver shaft 571. Preferably, cannular support portion 562 and guide support portion 561 are rigidly connected (e.g., single integral component or attached without allowing cannular support portion 562 to rotate relative guide support portion 561) to provide increased control of the orientation of cannula 574 and driver shaft 571 during use. Preferably, guide support portion 561 comprises hand grip 565 to help control, steer and/or orient the direction of cutting of reamer 596. Additionally, the guide arm 560 can be disconnected from the adaptor arm 556 with the quick connect 564 and 577 to facilitate introduction into or removal from the incision. Advantageously, this allows the guide arm 560 to be disconnected and/or re-connected to the adaptor arm 556 while the reamer device remains within the incision to eliminate having to remove the reamer and then re-insert the reamer for disconnecting/connecting the guide arm 560.

As also shown in FIG. 5B, preferably, guide arm 560 is configured to be removed from the adaptor shaft 551 and later re-connected without having to disconnect the adaptor head 595 from the reamer 596. Preferably, adapter shaft 571 comprises connector 552 to connect to a handle or grip or robotic arm (not shown). According to preferred embodiments, the guide support portion 561 is attached to shaft 551 adjacent connector 552, as shown in FIG. 5B.

Preferably, as shown in FIG. 5B, guide arm 560 is configured to be connected to the shaft 551 and the cannula 574 and/or driver shaft 571 to enable the entire assembly of the shaft 551 (including adaptor housing attached thereto) and guide arm 560 to be rotated around the axis of the driver shaft 571 and/or around the adaptor head 595 and/or reamer 596. Advantageously, this allows the user (not shown) to adjust the position of shaft 551 and/or guide arm 570 without changing the direction of the axis of the driver shaft 571 and/or cutting orientation of the reamer 596. As shown in FIG. 5B, shaft 551 comprises elbow 555 providing an offset 556 of shaft 551 relative to adaptor head 595 and/or reamer 596 to provide increased range of motion.

Another aspect of the invention relates to methods of using the adaptor tools, adaptor devices and adaptor systems described herein.

One embodiment of the invention relates to method of performing arthroplasty, the method comprising:
 (a) connecting an adaptor device, preferably as described herein, to a reamer;
 (b) inserting adaptor device connected to reamer into the bony anatomy;
 (c) connecting a reamer driver to the adaptor device to engage the reamer;

(d) rotating the reamer with the reamer driver thereby cutting bone; and
(e) changing the orientation of the reamer relative to the reamer driver using the adaptor device.

Another embodiment of the invention relates to a method of performing arthroplasty, the method comprising:
(a) inserting a reamer into a bony anatomy;
(b) connecting an adaptor device, preferably as described herein, to the reamer;
(c) connecting a reamer driver to the adaptor device to engage the reamer;
(d) rotating the reamer with the reamer driver thereby cutting bone; and
(e) changing the orientation of the reamer relative to the reamer driver using the adapter device.

Another embodiment of the invention relates to a method of performing arthroplasty, the method comprising:
(a) connect a handle having a handle end to an adaptor device, preferably as described herein;
(b) connect the adaptor device to a reamer;
(c) insert the handle end, the adaptor device and reamer into bony anatomy;
(d) insert a driver into the adaptor device or otherwise engage the adapter device with the driver;
(e) rotate the driver to rotate the reamer via the adaptor device;
(f) reposition the handle to re-orient the reamer while the reamer is inserted in the bony anatomy;
(g) stop rotating the driver;
(h) remove the driver from the adaptor device; and
(i) remove the handle end, the adaptor device and the reamer from the bony anatomy.

Preferably, the rotation of the reamer is paused before the repositioning and re-started after the repositioning.

Preferably, the remove step (i) comprises:
disconnecting the adaptor device from the reamer and removing the adaptor device and the handle from the bony anatomy; and
removing the reamer from the bony anatomy.

Another embodiment of the invention relates to a method of performing arthroplasty, the method comprising:
(a) insert a reamer into bony anatomy;
(b) connect a handle having a handle end to an adaptor device, preferably as described herein;
(c) connect the adaptor device to the reamer;
(d) insert a driver into the adaptor device or otherwise engage the adapter device with the driver;
(e) rotate the driver to rotate the reamer via the adaptor device;
(f) reposition the handle to re-orient the reamer while the reamer is inserted in the bony anatomy;
(g) stop rotating the driver;
(h) remove the driver from the adaptor device; and
(i) remove the handle end, the adaptor device and the reamer from the bony anatomy.

Preferably, the rotation of the reamer is paused before the repositioning and re-started after the repositioning.

Preferably, the remove step (i) comprises:
disconnecting the adaptor device from the reamer and removing the adaptor device and the handle from the bony anatomy; and
removing the reamer from the bony anatomy.

FIGS. 6A-B shows the ball nosed reamer driver configured to engage the reamer adaptor to rotate the reamer (or "reamer basket"). FIG. 6A is a side view of the adaptor tool 601 including an adaptor device 610 connected to reamer 650 which is adjacent bony hip anatomy 660 and positioned for reaming and including adaptor head recess 611 configured to be engaged with ball nosed reamer driver tip 622 of driver shaft 621 connected to electric hand driver 620. The reamer driver shaft 621 can be inserted through a cannula if required, as shown in FIG. 5. FIG. 6B is a close-up view of FIG. 6A showing ball nosed reamer driver tip 622 adjacent the adaptor head recess 611 configured to be engaged by tip 622.

FIG. 6C shows a side view of the reamer driver shaft 621 connected to power device 620 with driver tip 622 inserted into adaptor device 610 to drive the reamer 650 to cut and/or abrade the bony hip anatomy 660 by a reaming mechanism. In this view, the reamer driver shaft 621 is in line with the reamer adaptor device 610 and reamer 650.

Figure 7:
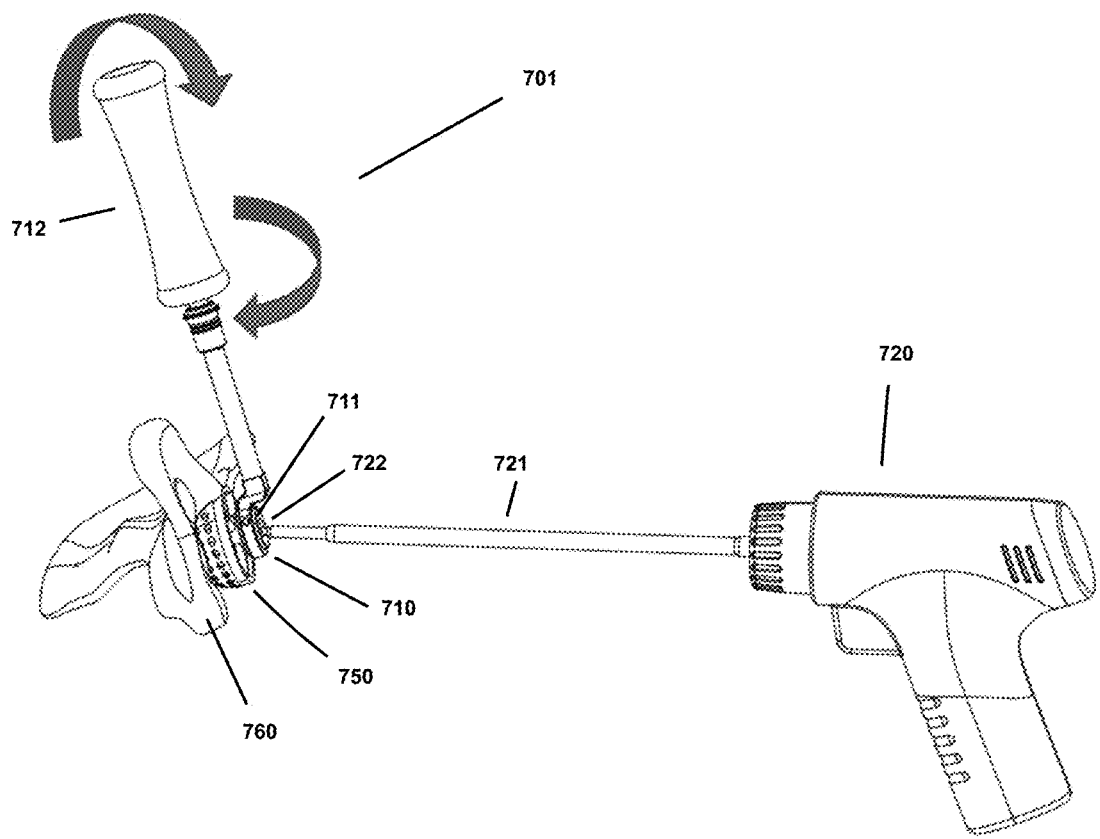
FIG. 7 is a side illustration of the reamer system shown in FIGS. 6A-C showing the reamer possible orientation adjustments (shown by arrows) using the adaptor handle.

FIG. 7 is a side view of the adaptor tool 701 including an adaptor device 710 connected to reamer 750 which is adjacent bony hip anatomy 760 and positioned for reaming and including adaptor head recess 711 configured to be engaged with ball nosed reamer driver tip 722 of driver shaft 721 connected to electric hand driver 720. FIG. 7 shows how the reamer orientation can be adjusted in all planes via the adaptor handle 712, that is by manipulating the handle 712. FIG. 7 also shows how the preferred ball nosed reamer driver tip 722, for example, accommodates "out of line" alignment of the driver shaft relative to the reamer. This allows the "direction" of the reaming being performed on the bony anatomy to be changed relative to the driver shaft 721.

Figure 9A:
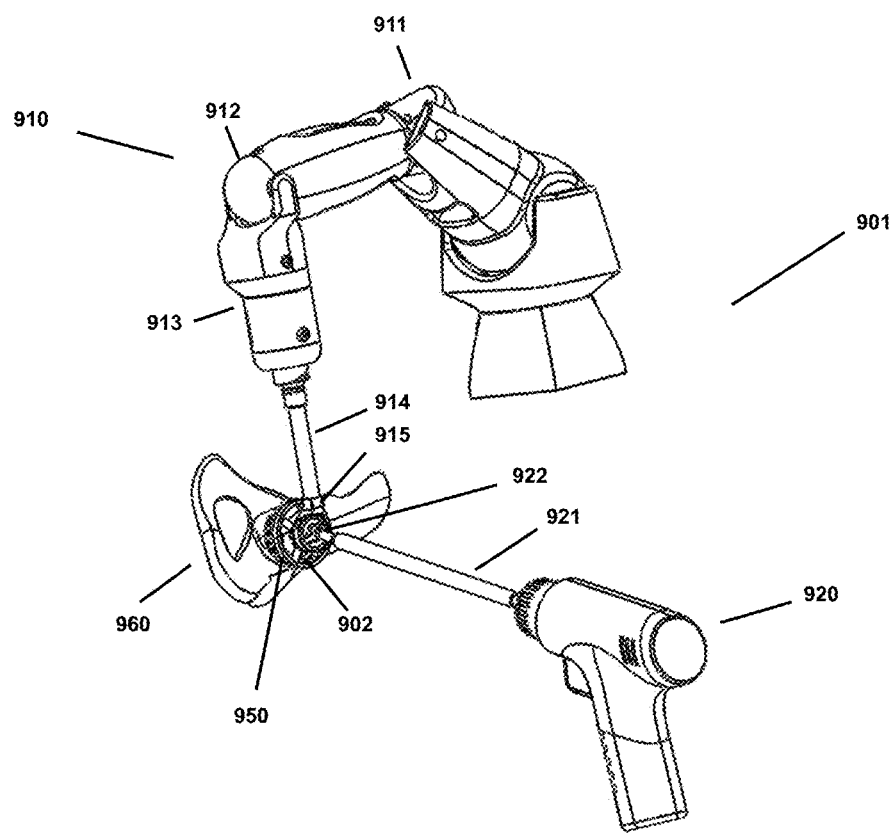
FIG. 9A is a side perspective illustration of a reamer system including a robotic arm to hold, orientate, direct, and, optionally, drive/rotate the reamer or reamer shaft.

FIG. 9A is a side perspective illustration of a reamer system 901 including a robotic arm 910 to hold, orientate, and direct the reamer 950 (via connecting shaft 914 via robotic arm connector 915). Reamer 950 is shown adjacent bony hip anatomy 960. Adaptor device 902 houses reamer 950 which is shown in contact with driver tip 922 of driver shaft 921 connected to electric hand driver 920.

Figure 9B:
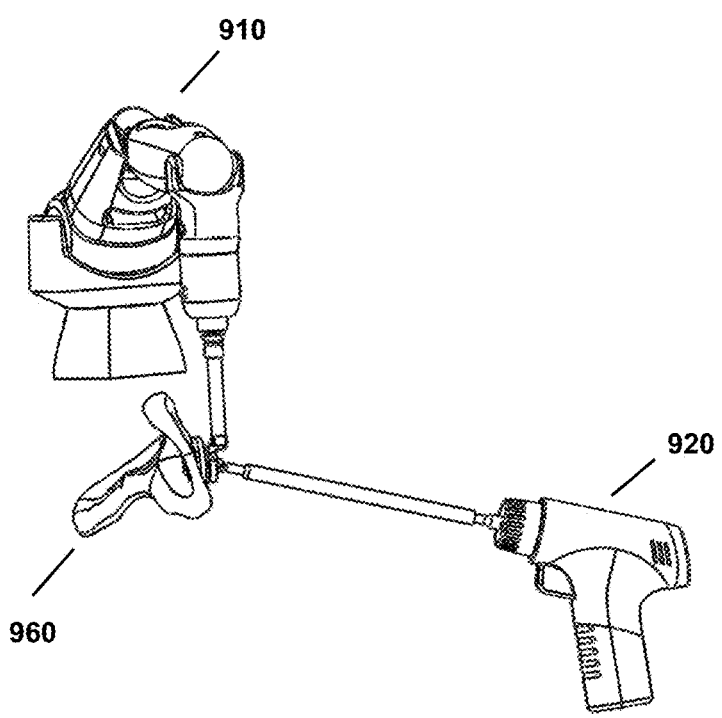
FIG. 9B is a side view of the reamer system of FIG. 9A.

Preferably, robotic arm 902 has at least a first elbow joint 911 and second elbow joint 912 and a rotational joint 913 to facilitate connection of robotic arm 902 to the adaptor device 902 and direct the orientation and direction of reamer 950. FIG. 9B is a side view of the reamer system of FIG. 9A.

According to alternative embodiments, the robotic arm includes an electric driver to drive the reamer (e.g., instead of using an electric hand driver shown in FIG. 9A). Preferably, the distal end of the robotic arm is configured to connect to the adaptor device and comprises an electric driver to drive the reamer. Preferably, the robotic arm connector comprises a component to attach to the adaptor housing and driver component to drive the reamer.

According to alternative embodiments, the system comprises a second robotic arm including an electric driver to drive the reamer while the first robotic arm is connected to the adaptor device.

One further embodiment of the invention relates to a robotic arm connector (or robotic arm adaptor) comprising a first end adapted to connect to the robotic arm and a second end adapted to connect to an adaptor device (as described herein). Preferably, the robotic arm connector allows the use of robotic arm not specifically configured for use with the adaptor devices described herein (e.g., a Stryker or Mako Robotic arm).

Alternative embodiments of the invention relate to a robotic arm connector comprising a first end adapted to connect to the robotic arm and a second end adapted to connect to a shaft connected to the adaptor housing.

According to another preferred embodiment the robotic arm or robotic arm connector has a distal end comprising an adaptor housing as described herein and configured to allow the adaptor head to be inserted into the adaptor housing. For example, the distal end of the robotic arm or distal end of the robotic arm connector comprises the adaptor device configured to reversibly connect to a reamer or other cutting tool, for example, configured to allow a reamer to be inserted into the adaptor housing at the distal end of the robotic arm.

Another embodiment of the invention relates to a reamer system comprising a robotic system to support a reaming tool. Preferably, the system comprises an arm configured to connect to and/or support the electric hand driver and also connect to a driver shaft that comprises the driver tip and is configured to connect to the adaptor device, as shown in FIG. 10, for example. FIG. 10 is a side view of reamer system 1000 comprising the robotic arm 910 of FIG. 9 and a second robotic support system 1010 configured to support a reaming tool 1009 comprising electric driver 1020 engagingly connected (directly or indirectly) to driver shaft 1030 which in turn is connected to reamer adaptor 1040 holding reamer 1050. Robotic support system 1010 comprises base 1012 and support arm 1011 connected to base 1012 and extending therefrom. Support arm 1011 is preferably rotatably connected to base 1012 at rotating connector 1013. Preferably, robotic arm 1011 has at least a first elbow joint 1012, second elbow joint 1013 and a rotational joint 1014 to facilitate connection of robotic arm 1010 to driver shaft 1030 (or elongated tube 1024 holding driver shaft 1030) and movement and orientation of the driver shaft 1030 relative to the adaptor device 1040, reamer 1050 and/or bony hip anatomy 1060.

Support arm 1011 comprises a distal end 1015. Distal end 1015 is shown having a pass-through housing 1016 (or clasp or holder or bracket configured to hold or clasp or support driver shaft 1030) having a first side 1017 and opposing second side 1018 and an elongated tube 1024 passing through housing 1016 and providing a grip or handle for a user as shown in FIG. 10. Driver shaft 1030 passes through elongated tube 1024 and is reversibly connected to adaptor device 1040 which is reversibly connected to reamer 1050. Support arm 1010 supports the reaming tool and also allows for adjusting the direction and/or orientation of the reamer during use.

According to one preferred embodiment, housing 1016 is configured to open or un-clasp the driver shaft 1030 (or elongated tube 1024 holding driver shaft 1030) to allow for disconnecting robotic arm 1011 from reaming tool 1009. This configuration also preferably allows robotic arm 1011 to be connected or re-connected to the reaming tool 1009 in reverse (e.g., clasping the housing 1016 onto the driver shaft 1030).

According to one alternative embodiment, elongated tube 1024 is omitted and replaced with a housing 1016 modified to include an elongated section to form a grip or handle for a user (e.g., grip or handle is integral to housing 1016). Preferably, the elongated section extends from second side 1018 of housing 1016.

According to another alternative embodiment, electric driver 1020 is omitted and a motor (e.g., electric motor in electric driver 1020), driver means or other mechanism for rotating driver shaft 1030 is incorporated in housing 1016 or otherwise incorporated in robotic arm 1011 to rotate driver shaft 1030. Preferably, a first robotic arm is configured to control the orientation and/or direction of the reaming process, while a second robotic arm includes the driver to rotate the reamer during the reaming process.

Preferably, the adjustment of the reamer orientation can occur during the reaming process (e.g., turning of the reamer to cut/abrade bone) instead of stopping or pausing the reamer driver before adjusting the reamer. According to alternative embodiments, the reamer process is stopped or paused before the reamer is re-oriented and, preferably, re-started after re-orientation of the reamer.

Alternatively, the non-ball nosed driver could also be engaged with the adaptor handle should the user desire the reamer orientation be in line with the driver shaft. That is, a driver could be aligned with the axis of the adaptor if the user did not want independent range of motion with the reamer.

The scope of the present devices, systems and methods, etc., includes both means plus function and step plus function concepts. However, the claims are not to be interpreted as indicating a "means plus function" relationship unless the word "means" is specifically recited in a claim, and the claims are to be interpreted as indicating a "means plus function" relationship where the word "means" is specifically recited in a claim. Similarly, the claims are not to be interpreted as indicating a "step plus function" relationship unless the word "step" is specifically recited in a claim, and the claims are to be interpreted as indicating a "step plus function" relationship where the word "step" is specifically recited in a claim.

Although several aspects of the invention have been disclosed in the foregoing specification, it is understood by those skilled in the art that many modifications and other aspects of the invention will come to mind to which the invention pertains, having the benefit of the teaching presented in the foregoing description and associated drawings. It is thus understood that the invention is not limited to the specific aspects disclosed hereinabove, and that many modifications and other aspects are intended to be included within the scope of the appended claims. Moreover, although specific terms are employed herein, as well as in the claims that follow, they are used only in a generic and descriptive sense, and not for the purposes of limiting the described invention.

What is claimed is:

1. An adaptor device for a bone cutting system, the adaptor device comprising:
   (a) an adaptor head configured to reversibly connect to a bone cutter and further configured to reversibly engage with a bone cutter driver;
   (b) an adaptor housing configured to connect to the adaptor head and further configured to attach to a handle for the adaptor device and/or to attach to a robotic arm configured to connect to the adaptor device; and
   (c) a handle connected to the adaptor housing or a robotic arm connected to the adaptor housing,
   wherein the handle or robotic arm comprises a grip and a shaft and the shaft is connected to the adaptor housing and wherein the grip is connected to the shaft using a quick connect.

2. The adaptor device of claim 1, wherein the bone cutter is configured for cutting a hemispherical cavity in bone.

3. An adaptor device for an arthroplasty reaming system, the adaptor device comprising:
   (a) an adaptor head configured to reversibly connect to a reamer and further configured to reversibly engage with a reamer driver; and
   (b) an adaptor housing configured to connect to the adaptor head and further configured to attach to a handle for the adaptor device and/or to attach to a robotic arm configured to connect to the adaptor device, wherein the adaptor housing comprises a ring-like structure to hold the adaptor head and the adaptor head can rotate within the ring-like structure and wherein the adaptor housing connects to the adaptor head using a quick release connection.

4. The adaptor device of claim 3, wherein the adaptor housing comprises a handle adaptor configured to connect to a handle or a robotic arm adaptor configured to connect to the robotic arm.

5. The adaptor device of claim 4, wherein the handle adaptor comprises a recess for receiving a shaft of the handle or the robotic arm adaptor comprises a recess for receiving a portion of the robotic arm.

6. The adaptor device of claim 3, wherein the adaptor head includes a reamer driver seat configured to engage the reamer driver.

7. The adaptor device of claim 6, wherein the adaptor head has a first side comprising one or more structures to engage the reamer and a second side comprising the reamer driver seat.

8. The adaptor device of claim 7, wherein the reamer driver seat is a recess adapted to engage the reamer driver.

9. The adaptor device of claim 7, wherein the reamer driver comprises a ball nosed tip.

10. The adaptor device of claim 9, wherein the ball nosed tip is configured to engage the reamer driver seat at variable angles in all planes.

11. The adaptor device of claim 3, wherein the adaptor device is configured for independent orientation of the reamer relative to the reamer driver in all planes.

12. The adaptor device of claim 3, further comprising a handle connected to the adaptor housing or a robotic arm connected to the adaptor housing.

13. The adaptor device of claim 12, wherein the adaptor device further comprises the handle and the handle comprises a grip and a shaft and the shaft is connected to the adaptor housing.

14. The adaptor device of claim 13, wherein the grip is connected to the shaft using a quick connect.

15. The adaptor device of claim 3, wherein the adaptor head comprises a first side comprising one or more structures to engage the reamer.

16. The adaptor device of claim 15, wherein said one or more structures are configured to mate with different types of reamers.

17. The adaptor device of claim 15, wherein said one or more structures are configured to snap into place onto the reamer.

18. A method of performing arthroplasty, the method comprising:
(a) connecting the adaptor device of claim 3 to a reamer;
(b) inserting the adaptor device connected to the reamer into a bony anatomy;
(c) connecting a reamer driver to the adaptor device to engage the reamer, wherein the reamer has an orientation relative to the reamer driver;
(d) rotating the reamer with the reamer driver thereby cutting bone; and
(e) changing the orientation of the reamer relative to the reamer driver using the adapter device.

19. An adaptor device for a bone cutting system, the adaptor device comprising:
(a) an adaptor head having a bottom side configured to reversibly connect to a bone cutter having a cutting direction and an opposing top side having a recess configured to reversibly engage with a bone cutter driver, wherein the bone cutter driver is configured to engage the top side of the adaptor head at variable angles in all planes; and
(b) an adaptor housing configured to connect to the adaptor head and configured to provide independent control of the cutting direction of the bone cutter relative to the bone cutter driver,
wherein the adaptor housing connects to the adaptor head using a quick release connection.

20. An adaptor device for an orthopedic surgical reaming system, the adaptor device comprising:
(a) an adaptor head having a bottom side configured to reversibly connect to a reamer having a direction of reaming and an opposing top side having a recess configured to reversibly engage with a reamer driver at variable angles; and
(b) an adaptor housing configured to connect to the adaptor head and configured to provide independent control of the direction of reaming of the reamer at variable angles relative to the reamer driver,
wherein the adaptor housing comprises an annular ring or C-shaped structure configured to hold the adaptor head and configured to allow the adaptor head to rotate within the adaptor housing.

21. The adaptor device of claim 20, further comprising a handle connected to the adaptor device and/or a robotic arm connected to the adaptor device.

22. The adaptor device of claim 20, wherein the adaptor housing is configured to connect to the adaptor head using a quick release connection.

* * * * *